United States Patent
Brierley et al.

(10) Patent No.: US 6,207,806 B1
(45) Date of Patent: *Mar. 27, 2001

(54) IGF-I PURIFICATION PROCESS

(75) Inventors: Russell A. Brierley, West Chester; Joan N. Abrams, Downingtown; John M. Hanson, Malvern; Francis C. Maslanka, Exton, all of PA (US)

(73) Assignee: Cephalon Inc., West Chester, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/851,162

(22) Filed: May 5, 1997

Related U.S. Application Data

(62) Division of application No. 08/422,436, filed on Apr. 14, 1995, now Pat. No. 5,650,496.

(51) Int. Cl.$^7$ .......................... C07K 14/475; C12N 15/18
(52) U.S. Cl. ....................... 530/416; 530/399; 530/408; 530/412
(58) Field of Search .................................... 530/303, 305, 530/399, 412, 416, 408

(56) References Cited

U.S. PATENT DOCUMENTS

| | | |
|---|---|---|
| 5,093,317 | 3/1992 | Lewis et al. ............................ 514/12 |
| 5,231,178 | 7/1993 | Holtz et al. ........................... 530/399 |
| 5,288,931 | 2/1994 | Chang et al. ......................... 530/399 |
| 5,324,639 | 6/1994 | Brierley et al. ...................... 435/69.4 |
| 5,407,810 | 4/1995 | Builder et al. ...................... 435/69.1 |
| 5,410,026 | 4/1995 | Chang et al. ......................... 530/408 |
| 5,446,024 | 8/1995 | Builder et al. ......................... 514/12 |
| 5,451,660 | 9/1995 | Builder et al. ....................... 530/344 |
| 5,459,052 | 10/1995 | Shriver et al. ....................... 435/71.2 |

FOREIGN PATENT DOCUMENTS

| | | |
|---|---|---|
| WO 93/11240 | 6/1993 | (WO) . |
| WO 93/19084 | 9/1993 | (WO) . |
| WO 95/06064 | 3/1995 | (WO) . |
| WO 95/16777 | 6/1995 | (WO) . |

OTHER PUBLICATIONS

Elliott et al., "Yeast–Derived Recombinant Human Insulin–Like Growth Factor I: Production, Purification, and Structural Characterization," *Journal of Protein Chemistry* 9(1):95–104 (1990).
Axellson et al., "Disulfide arrangement of human insulin–like growth factor I derived from yeast and plasma," *J. Biochem.* 206:987994 (1992).
Bayne et al., "Expression, purification and characterization of recombinant human insulin–like growth factor I in yeast," *Gene* 66:235–244 (1988).
Browning et al., "Disulfide Scrambling of Interleukin–2: HPLC Resolution of the Three Possible Isomers," *Analytical Biochemistry*, 155:123–128 (1986).
Chang et al., "Single–Step Solubilization and Folding of IGF–1 Aggregates from *Escherichia coli*," Chapter 14, in *Protein Folding In Vivo and In Vitro*, Am Chem. Soc., pp. 178–188 (1993).
Chang et al., "Folding of IGF–I," BIOT, Abstract #117.
Hart et al., "Effect of environment on insulin–like growth factor I refolding selectivity," *Biotechnol. Appl. Biochem* 20:217–232 (1994).
Hart et al., "Large Scale, *In Situ* Isolation of Periplasmic IGF–I from *E. coli*," *Bio/Technology* 12:1113–1117 (1994).
Hejnaes et al., "Development of an optimized refolding process for recombinant Ala—Glu—IGF–1," *Protein Engineering*, 5:797–806 (1992).
Hober et al., "Disulfide Exchange Folding of Insulin–like Growth Factor I," *Biochemistry* 31:1749–1759 (1992).
Meng et al., "Reduction Studies on Bacterial Recombinant Somatomedin C Insulin–Like Growth Factor–1," *Journal of Chromatography* 443:183–192 (1988).
Miller et al., "Oxidative Refolding of Insulin–like Growth Factor 1 Yields Two Products of Similar Thermodynamic Stability: A Bifurcating Protein–Folding Pathway," *Biochemistry* 32:5203–5213 (1993).
Niwa et al., "Chemical Synthesis, Cloning and Expression of Genes for Human Somatedin C (Insulin–like Growth Factor I) and $^{59}$Val—Somatomedin C," *Ann. NY Acad. Sci.* 469:31–52 (1986).
Olson et al., "Perparative isolation of recombinant human insulin–like growth factor 1 by reversed–phase high–performance liquid chromatography," *Journal of Chromatography A*, 675:101–112 (1994).
Petrides et al., "An Improved Method for the Purification of Human Insulin–Like Growth Factors I and II," *Endocrinology* 118:2034–2038 (1986).
Pfeifle et al., "Insulin–Like Factor 1/Somatomedin–C: Rapid Isolation Procedure With FPLC," *Preparative Biochemistry* 15:291–307 (1985).
Scrip No. 910, p. 21 (1984).
Steiner et al., "The Spontaneous Reoxidation of Reduced Beef and Rat Proinsulins," *Biochemistry* 60:622–629 (1968).
Sofer et al., BioTechniques Nov./Dec. 198–203, 1983.

*Primary Examiner*—Christine Saoud
(74) *Attorney, Agent, or Firm*—Fish & Richardson P.C.

(57) ABSTRACT

Disclosed is an improved process for obtaining purified, monomeric, intact, correctly-folded insulin-like growth factor-I (also known as somatomedin-C). The improvements, consisting primarily of the addition of an IGF-I unfolding/refolding step and the substitution of a reverse phase chromatography step for a gel filtration chromatography step result in a three-fold increase in final yield. The process includes the following steps, in order: first cation exchange, unfolding/refolding, hydrophobic interaction chromatography, second cation exchange, and reverse phase chromatography.

25 Claims, 12 Drawing Sheets

IGF-I PURIFICATION PROCESS

This is a division of application Ser. No. 08/422,436, filed Apr. 14, 1995 now U.S. Pat. No. 5,650,496.

FIELD OF THE INVENTION

This invention relates to protein purification.

BACKGROUND OF THE INVENTION

Insulin-like growth factor-I ("IGF-I;" also known as "somatomedin-C") is a mammalian growth factor essential for normal growth and development. It has insulin-like effects on muscle and adipose tissue, and it has mitogenic effects on several cell types. IGF-I has a variety of clinical uses. For example, it may be used to enhance the survival of neurons such as non-mitotic cholinergic neurons (Lewis et al, U.S. Pat. No. 5,093,317).

The complete amino acid sequence of the human IGF-I protein is known, and DNA encoding human IGF-I has been cloned and expressed in *E. coli* and yeast (see, e.g., Brierley et al., U.S. Pat. No. 5,324,639). The human IGF-I protein consists of a single 70-amino acid polypeptide that includes six cysteine residues, all of which participate in the formation of three intrachain disulfide bonds (Axelsson et al., *Eur. J. Biochem.* 206:987 (1992)). The three disulfide bonds, with all six cysteine residues properly paired, are necessary in order for IGF-I to have its correct (i.e., natural) tertiary structure. Upon reduction and reoxidation of the disulfide bonds, IGF-I can refold in various ways, forming as many as 15 monomeric configurations (Meng et al., *J. Chrom.* 433:183 (1988)). In addition, IGF-I polypeptides can interact with each other to form multimeric structures. Processes for obtaining purified, correctly folded IGF-I have been published (see, e.g., Holtz et al., U.S. Pat. No. 5,231,178 ("Holtz"); Chang et al., U.S. Pat. No. 5,288,931; and Hart et al., *Biotech. Appl. Biochem.* 20:217 (1994)).

SUMMARY OF THE INVENTION

We have discovered an improved process for obtaining purified, monomeric, intact, correctly-folded (i.e., "authentic") IGF-I. More particularly, we have discovered how to increase, by at least three-fold, the final yield of authentic IGF-I obtained in the IGF-I purification process described in Holtz (supra). The yield increase is obtained primarily by: (1) including an IGF-I protein unfolding/refolding step, carried out after the first cation chromotagraphy step; and (2) substituting a reverse phase chromotagraphy step for the gel filtration step described in Holtz.

Accordingly, the invention features a process for the purification of monomeric, intact, correctly-folded IGF-I polypeptide from a medium containing IGF-I polypeptides, said process comprising the steps of:

(a) contacting the medium with a sufficient quantity of a first cation exchange matrix under conditions allowing adsorption of at least about 95% of total IGF-I from the medium;

(b) washing the IGF-I-loaded first cation exchange matrix with a first cation exchange wash buffer, which removes a substantial amount of adsorbed non-IGF-I material without removing a substantial amount of authentic or non-authentic IGF-I;

(c) eluting all forms of adsorbed IGF-I from the cation exchange matrix of step (a) by contacting said cation exchange matrix with a sufficient quantity of a first cation exchange elution buffer, which has a sufficiently high pH or ionic strength to displace substantially all of said authentic and non-authentic IGF-I from said cation exchange matrix;

(d) transferring the IGF-I-containing eluate from step (c) into an unfolding/refolding buffer, which: (i) reduces the intrachain disulfide bonds of IGF-I protein and promotes unfolding without permanent denaturation; and (ii) permits refolding of the IGF-I and reoxidation to form properly-paired intrachain disulfide bonds;

(e) contacting the refolded IGF-I from step (d), after transfer into a suitable solvent system, with a sufficient quantity of a hydrophobic interaction chromatography matrix under conditions allowing adsorption of at least about 95% of said IGF-I from said eluate;

(f) washing the IGF-I-loaded hydrophobic interaction chromatography matrix with a hydrophobic interaction wash buffer having an ionic strength sufficiently low to remove most of the non-authentic IGF-I, but not so low as to remove a significant proportion of the authentic IGF-I from the hydrophobic interaction chromatography matrix;

(g) eluting the adsorbed IGF-I from said hydrophobic interaction chromatography matrix by contacting said matrix with a hydrophobic interaction elution buffer, which has a sufficiently elevated pH, or sufficiently low ionic strength, to cause displacement of substantially all of the adsorbed authentic IGF-I from said matrix;

(h) contacting the eluate from step (g) with a sufficient quantity of a second cation exchange matrix under conditions allowing adsorption of at least about 95% of the IGF-I from the eluate;

(i) washing the IGF-I-loaded second cation exchange matrix with a cation exchange wash buffer having a sufficiently high ionic strength, or sufficiently high pH, to remove a significant proportion of non-authentic IGF-I, but not so high as to remove a significant proportion of authentic IGF-I;

(j) eluting the adsorbed IGF-I from said second cation exchange matrix by contacting said matrix with a second cation exchange elution buffer, which has a sufficiently high ionic strength, or sufficiently high pH, to displace substantially all of the adsorbed authentic IGF-I from said matrix;

(k) contacting the eluate from step (j), in an aqueous buffer, with a suitable quantity of a reverse phase chromatography matrix under conditions allowing adsorption of at least about 95% of the IGF-I from the eluate;

(l) washing the IGF-I-loaded reverse phase chromatography matrix with an aqueous/organic reverse phase wash buffer having an organic solvent concentration sufficiently high to remove a substantial proportion of non-authentic IGF-I, but not so high as to remove a significant proportion of authentic IGF-I;

(m) eluting the adsorbed IGF-I from said reverse phase chromatography matrix with an aqueous/organic buffer having an organic solvent concentration high enough to remove substantially all of the authentic IGF-I without removing a significant proportion of multimeric forms of IGF-I.

Optionally, the non-authentic IGF-I recovered from step (f) is reprocessed at least once through steps (d) to (g), inclusive, before initiation of step (h).

As used herein, the term "authentic" IGF-I means monomeric, intact, correctly folded IGF-I, with three intrachain disulfide bonds involving properly paired cysteine residues, i.e., paired as in naturally-occurring IGF-I.

As used herein, the term "column volume" means the volume occupied by a chromatography matrix, including interstitial liquid.

As used herein, the term "degraded" IGF-I means IGF-I in which one or more of the covalent bonds present in the polypeptide backbone or the amino acid side chains of authentic IGF-I have been cleaved.

As used herein, "des-2" IGF-I means IGF-I missing the first two amino acid residues of authentic IGF-I.

As used herein, the term "glycosylated" IGF-I means IGF-I with one or more covalently attached carbohydrate moieties.

As used herein, the term "intact" IGF-I means IGF-I that is not degraded.

As used herein, the term "misfolded" IGF-I means IGF-I whose secondary structure is other than that of authentic IGF-I.

As used herein, the term "multimeric" IGF-I means two or more IGF-I polypeptide chains linked by covalent or non-covalent chemical bonds.

As used herein, the term "oxidized" IGF-I means IGF-I containing at least one oxidized amino acid residue.

As used herein, the term "reoxidized" IGF-I means IGF-I in which one or more intrachain disulfide bonds have reformed, following cleavage of those bonds.

As used herein, the term "about" in reference to a numerical value means ±10% of the value, e.g., "about 50%" means between 45% and 55%.

DETAILED DESCRIPTION OF THE INVENTION

Figure 1:
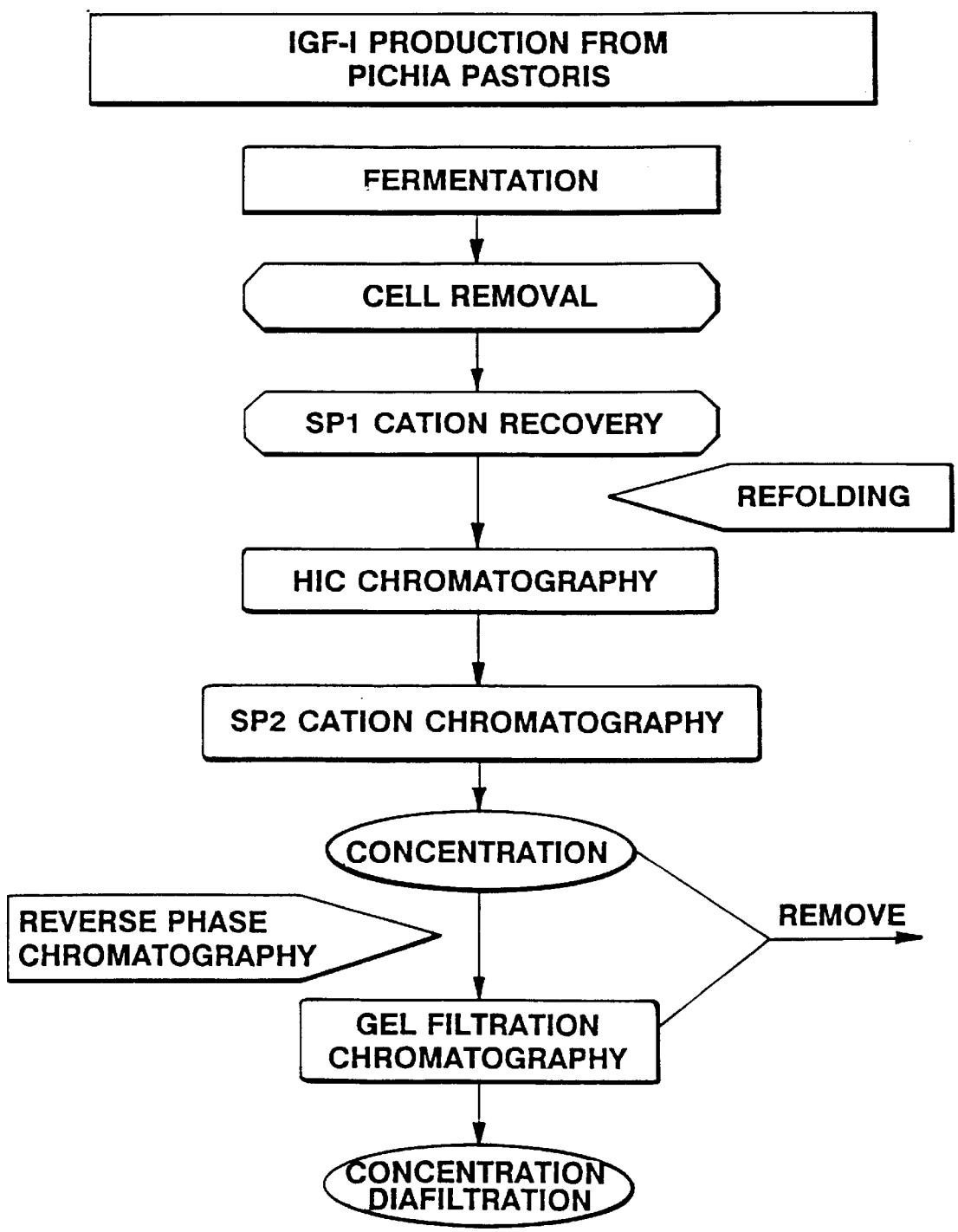
FIG. 1 is a flow chart comparing the steps of the Holtz process with the steps of an embodiment of the invention.

The invention provides an improved process for the purification of monomeric, intact, correctly-folded IGF-I.

IGF-I Starting Material and Cell Removal

The IGF-I starting material with which the invention is practiced may be in a medium contaminated with various salts, acids, bases, organic small molecules, non-protein macromolecules, non-IGF-I proteins, IGF-I fragments, multimeric IGF-I, incorrectly folded IGF-I, or any combination of the foregoing. The IGF-I may be from natural sources or it may be recombinant IGF-I produced by genetically transformed eukaryotic cells. In a preferred embodiment, the IGF-I is recombinant IGF-I produced by genetically transformed yeast. In a particularly preferred embodiment, the recombinant IGF-I is produced in Pichia pastoris strain GS115 (NRRL Y-15851) stably transformed with expression vector pIGF201, pIGF202, pIGF204 or pIGF206. The production of IGF-I in P. pastoris strain GS115, using expression vectors pIGF201, pIGF202, pIGF204 and pIGF206 is described in Brierley et al., U.S. Pat. No. 5,324,639, which is here incorporated by reference.

Preferably, this invention is practiced with recombinant IGF-I that is secreted from transformed yeast cells. Secretion by yeast cells results when the yeast cells have been transformed with an IGF-I expression vector that encodes an IGF-I precursor protein comprising an N-terminal signal peptide. The signal peptide causes the IGF-I precursor protein to be secreted through the plasma membrane of the yeast cell into the growth medium. During the secretion process, the signal peptide is cleaved to yield the mature IGF-I polypeptide.

When the invention is practiced with recombinant yeast cells, the IGF-I is secreted into the medium during a fermentation process. Particularly preferred fermentation steps/processes are described in U.S. Pat. No. 5,324,639. Using the particularly preferred fermentation as set forth in U.S. Pat. No. 5,324,639, the amount of "PTM1" trace salts added during fermentation can be beneficially reduced approximately 10-fold, to a single addition of 2 ml per liter starting medium. Preferably, the levels of sulfuric acid, copper, zinc and iron in the "PTM1" is reduced 3-fold in comparison to the process described in the U.S. Pat. No. 5,324,639.

When the invention is practiced with recombinant secreted IGF-I, the host cells must be removed from the IGF-I-containing medium. Cell removal may be by any suitable means, e.g., centrifugation or microfiltration, or both.

First Cation Exchange Step

Following host cell removal, the first step in the process of this invention is contacting an IGF-I-containing sample solution with a suitable quantity of a first cation exchange matrix under conditions allowing adsorption of at least about 95% of the total IGF-I from the solution.

The IGF-I-containing solution may be contacted with the first cation exchange matrix in various ways. For example, the first cation exchange matrix may be in a vessel into which the IGF-I-containing medium is introduced, followed by decanting of the IGF-I-depleted medium from the first cation exchange matrix. Alternatively, the first cation exchange matrix can be added to the vessel containing the IFG-I-containing medium, followed by removal of IGF-I-depleted solution from first cation exchange matrix. Preferably, the first cation exchange matrix is in a column through which the IGF-I-containing medium is allowed to flow.

Matrices that may be used in the first cation exchange step are well known in the art. Preferably, the cation exchange matrix is compatible with a high flow rate, i.e., able to withstand high pressures, possesses a macroporous structure, and is capable of binding IGF-I over a wide pH range. Matrix supports such as cellulose, polystyrene, dextrans, agarose, cross-linked agarose, and the like, may be used for the cation exchange matrix. Preferred cation exchange matrices for use in this step are sulfylpropylated ("SP") matrices. A particularly preferred first cation exchange matrix is Toyopearl SP550C™ (TosoHaas, Philadelphia, Pa.).

One of ordinary skill in the art is credited with recognizing that prior to contacting the IGF-I-containing sample solution with the first cation exchange matrix, the matrix may need to be regenerated and/or activated. Regeneration and/or activation should be carried out according to the recommendations of the matrix vendor and methods known in the art.

The quantity of first cation exchange matrix material used is typically at least about 0.031, to 1.0 liter of matrix per gram of authentic IGF-I. Typically the IGF-I-containing solution is contacted with the first cation exchange matrix for about 0.01 to 1 hour, or longer, at a temperature of about 20 to 30° C. A temperature of about 20° to 25° C. is preferred.

Once the IGF-I-containing solution has been contacted with the first cation exchange matrix to allow IGF-I adsorption, the IGF-I-depleted solution is removed. This can be done in various ways, e.g., filtration, decantation, centrifugation, and the like. In a preferred embodiment, contacting of the IGF-I-containing solution and removal of the IGF-I-depleted medium are done in one step by passing the IGF-I-containing medium through a chromatography column comprising the first cation exchange matrix.

Once the IGF-I has been adsorbed onto the first cation exchange matrix, and prior to IGF-I elution, it is preferable to wash the IGF-I-loaded matrix with about 1 to 10 column volumes of a dilute, weak acid. Exemplary dilute, weak acid solutions include acetic acid or phosphoric acid solutions, at a concentration of about 0.02 M.

In some previously described processes, the IGF-I-loaded first cation exchange column is further washed with a dilute weak acid (or buffer) containing salt, e.g., 0.1 M sodium chloride, to remove impurities, including multimeric and/or misfolded monomeric forms of IGF-I, that are bound less tightly to the first cation exchange matrix than is IGF-I. In the present invention, such high ionic strength washing steps are avoided in the first cationic exchange step, because it is advantageous to recover multimeric or misfolded monomeric forms of IGF-I, which can be converted to authentic IGF-I in the subsequent unfolding/refolding step, thereby increasing overall yield of authentic IGF-I.

A particularly preferred washing procedure for the first cationic exchange step is the following sequence: approximately 3.0 column volumes of 0.02 M acetic acid; followed by approximately 3.0 column volumes of 0.05 M sodium acetate (pH 5.5).

Once the IGF-I-loaded first cation exchange matrix has been washed (as described above), the IGF-I is eluted by contacting the matrix with a sufficient quantity of a solvent system ("elution buffer") which has a sufficiently high pH or ionic strength to displace substantially all of the IGF-I from the matrix.

The elution buffer should comprise a buffering agent suitable for maintaining a pH in the range of 5.0 to 7.0, and a salt concentration of about a 0.2 to 1.0 M. A preferred elution buffer consists of 0.05 M sodium acetate (pH 5.5) and 0.4 M sodium chloride.

The quantity of elution buffer used is variable but is preferably between 3 and 10 column volumes. When the elution buffer consists of 0.05 M sodium acetate (pH 5.5) and 0.4 M sodium chloride, the preferred elution buffer quantity is four column volumes.

Elution of IGF-I from the cation exchange matrix can be done under various conditions. Preferably, a temperature of about 2° to 30° C. is employed. Preferably, elution time is relatively short, i.e., about 0.01 to 1.0 hour, although longer or shorter times may be employed.

IGF-I Unfolding/Refolding Step

An essential feature of this invention is the inclusion of an IGF-I unfolding/refolding step following the first cation exchange step. For the unfolding/refolding step, the cation exchange eluate is transferred into a buffer that promotes disulfide bond exchange ("unfolding/refolding buffer"). Such transfer may be by any of various means, including dilution, gel filtration, dialysis, or diafiltration.

The unfolding/refolding buffer may be generally characterized as alkaline, weakly reducing, weakly denaturing and solubilizing. The buffer must be able to: (1) reduce the intrachain disulfide bonds of the IGF-I and promote unfolding of the IGF-I protein without permanent denaturation; and (2) permit refolding of the IGF-I with reoxidation to form properly-paired IGF-I intrachain disulfide bonds.

Preferably, the unfolding/refolding buffer contains a buffering agent suitable for maintaining the pH at between 8.0 and 10.5, e.g., borate, acetate, tris-hydroxy methyl amino methane ("tris"); a chaotropic agent, e.g., urea or guanidine; a salt, e.g., sodium chloride, ammonium sulfate, sodium sulfate; an alcohol, e.g., methanol, ethanol, 2-propanol; and a reducing agent, e.g., dithiothreitol ("DTT"), cysteine, β-mercaptoethanol ("BME"). Preferably, the unfolding/refolding buffer has a pH of between 8.5 and 10.0 and comprises urea at a concentration of 1.5 to 3.0 M, sodium chloride at a concentration of 1.0 to 3.0 M, ethanol at a concentration of 5 to 20% (v/v), sodium borate at a concentration of 1 mM to 15 mM, and dithiothreitol at a concentration of 0.005 mM to 10 mM. Most preferably, the pH of the unfolding/refolding buffer is between approximately 9.0 and 9.5 and the buffer consists of 2 M urea, 1.5 mM sodium chloride, 15% ethanol, 5 mM sodium borate and 0.2 mM DTT.

Preferably, the total IGF-I concentration is between about 0.1 and 5 mg/ml; more preferably, this concentration is between 0.2 and 2 mg/ml.

Preferably, the composition of the unfolding/refolding buffer and the concentrations of the components are such that the refolding and reoxidation begins within one hour of the unfolding and reduction, and is essentially complete within 4 to 40 hours. More preferably, the refolding and reoxidation is essentially complete within 15 to 20 hours.

When the most-preferred unfolding/refolding buffer (described above) is used, disulfide reduction may occur within seconds. With gentle stirring in the presence of air, at room temperature, reoxidation may begin within approximately one hour. Refolding and reoxidation is essentially complete within approximately 15 to 20 hours.

Hydrophobic Interaction Chromatography (HIC) Step

Following the unfolding/refolding step, the partially purified and refolded IGF-I is contacted with a sufficient quantity of an HIC matrix, to adsorb at least about 95% of the IGF-I. Preferably, the HIC matrix is in a column through which the IGF-I-containing buffer is passed.

Prior to contacting a solution of refolded IGF-I with the HIC matrix, the pH and salt concentration of the IGF-I-containing sample is adjusted. Preferably, the pH is adjusted to between 4.0 and 5.0, and the salt concentration is adjusted to between 0.4 M and 2.0 M. More preferably the pH is adjusted to between 4.0 and 4.5, and the salt concentration is adjusted to between 1.0 and 1.5 M.

Increasing the salt concentration of the IGF-I-containing medium promotes the binding of IGF-I to the HIC matrix. Salts suitable for such use include sodium sulfate, potassium sulfate, ammonium sulfate, potassium phosphate, sodium acetate, ammonium acetate, sodium chloride, sodium citrate and the like.

HIC matrices suitable for use in this invention are alkyl- or aryl-substituted HIC matrices. Exemplary HIC matrices include butyl-, octyl-, or phenyl-substituted matrices. HIC matrix supports useful in the practice of the present invention include synthetic polymers, e.g., polystyrene, poly (methacrylates), etc.; cellulose, dextrans, agarose, cross-linked agarose, and the like. A particularly preferred HIC matrix is a butyl-substituted, polymethacrylate hydrophobic interaction chromatography matrix (e.g., Toyopearl Butyl 650M™ or Toyopearl Butyl 650C, TosoHaas, Philadelphia, Pa.).

After any necessary regeneration, the column is equilibrated with 5 to 10 column volumes of a salt-containing acetate/phosphate buffer having a pH of about 2.5 to 4.5, and preferably about 3.0.

The quantity of HIC matrix used in the practice of this invention may vary. Typically, about 0.05 to 1 liter of matrix per gram of authentic IGF-I is used.

Typically, the IGF-I is contacted with the HIC matrix for at least about 0.1 to 30 minutes, with a temperature of about 15° to 30° C. A temperature between 20° and 25° C. is preferred.

Once substantially all of the IGF-I has been adsorbed by the first HIC matrix, the matrix is contacted (i.e., "washed") with a buffer that removes a significant quantity of contaminating material (i.e., material other than monomeric, intact, correctly-folded IGF-I) from the matrix, without removing significant quantities of the intact, monomeric, correctly-folded form of adsorbed IGF-I.

In a particularly preferred column washing procedure, the HIC column is washed with approximately three column volumes of 0.2 M acetic acid, containing 0.5 M sodium chloride. The HIC column is then washed with approximately ten column volumes of 0.2 M acetic acid, containing 0.15 to 0.25 M sodium chloride.

Upon completion of the column washing procedure, the HIC matrix is contacted with an HIC elution buffer, i.e., a buffer suitable for removing substantially all of the remaining adsorbed authentic IGF-I from the matrix.

The adsorbed IGF-I may be eluted from the HIC matrix under various conditions. Preferably, the elution buffer temperature is between 15° and 30° C. More preferably, it is between 20° and 25° C. Elution time will vary as a function of column dimensions, matrix material, and the like. Flow of eluent through the column is preferably about 10 to 300 cm/h.

A particularly preferred HIC elution procedure consists of applying approximately four column volumes of 0.2 M acetic acid, containing 0 to 0.02 M sodium chloride.

An HIC step including the particularly preferred materials and procedures described has several advantages over prior art processes: (1) it avoids potential IGF-I precipitation associated with impurities in ammonium sulfate; (2) it is more simple, by virtue of avoiding a salt gradient; and (3) pH changes are avoided.

Optionally, part, or all, of the eluate from the HIC matrix may be subjected to a second round of HIC purification. Optionally, part, or all, of the wash from the HIC matrix may be subjected to unfolding/refolding, followed by a second round of HIC.

Second Cation Exchange Step

The partially purified IGF-I obtained from the HIC step is subjected to a second cation exchange purification step. The principles involved in the selection of materials and procedures in the second cation exchange step are essentially the same as those in the first cation exchange stem. Accordingly, the same type of cation exchange matrix is typically used in the first and second cation exchange steps. In the most preferred embodiment of the invention, the second cation exchange step includes the following procedures.

A cation exchange column, preferably an SP column, and most preferably a Toyopearl SP550C™, SP650S™, or CM650M™ (TosoHaas) column, (previously regenerated) is equilibrated with a buffer consisting essentially of 0.05 M sodium acetate buffer (pH 5.5). After the partially purified IGF-I obtained from the HIC step is loaded onto the cation exchange column, the column is preferably washed with 7–10 column volumes of 0.05 M sodium acetate buffer (pH 5.5) containing 0.1 M NaCl. The IGF-I is then preferably eluted in approximately 7 column volumes of 0.05 M sodium acetate buffer (pH 5.5) containing 0.4 M sodium chloride.

The amount of second cation exchange matrix used, i.e., the size of the second cation exchange column will depend on the total amount of IGF-I to be adsorbed onto the matrix. The capacities of the various commercially available cation exchange matrices are provided by the commercial vendors, and the calculation of the proper ratio of matrix to IGF-I is within the level of ordinary skill in the art.

Reverse Phase Chromatography Step

The partially purified, refolded IGF-I obtained from the second cation exchange step is subjected to a reverse phase chromatography step. At a corresponding point in previously described methods for IGF-I purification, a gel filtration chromatography has been used. Gel filtration removes high molecular weight contaminants. The reverse phase chromatography of the present invention likewise removes high molecular weight contaminants. In addition, however, the reverse phase chromatography step removes various non-authentic forms of IGF-I, including oxidized, glycosylated, and partially degraded forms.

Various reverse phase chromatography media, which are commercially available, may be used. Polymer resin media are preferred. Among the advantages of polymer resin media is chemical stability that allows depyrogenation and sanitation with sodium hydroxide. A particularly preferred reverse phase chromatography medium is Amberchrom CG1000sd™ (TosoHaas, Philadelphia, Pa.). Exemplary organic solvents for use in the reverse phase chromatography step are methanol, ethanol, 2-propanol, and acetonitrile. Ethanol is particularly preferred.

The partially purified IGF-I sample obtained from the second cation exchange step is loaded onto the reverse phase column, after the column has been equilibrated with 0.2 M acetic acid.

The reverse phase column, with adsorbed IGF-I, is then washed with one or more aqueous/organic buffers, containing from 0% to 20% ethanol, to remove contaminating material, i.e., material other than authentic IGF-I. In a particularly preferred embodiment of the invention, the IGF-I-loaded reverse phase chromatography column is subjected to a first isocratic wash with approximately one column volume of 0.2 M acetic acid. The column is then subjected to a second isocratic wash with 19% ethanol in 0.2 M acetic acid, to remove contaminants less hydrophobic than authentic IGF-I (e.g., oxidized, glycosylated and some partially degraded, e.g., des-2 IGF-I, forms of IGF-I).

Authentic IGF-I is recovered through isocratic elution with an aqueous/organic buffer, followed by gradient elution. The isocratic elution is carried out with several column volumes of an aqueous/organic buffer, having an organic solvent concentration of between approximately 20% and 40%. Further IGF-I elution is carried out with an organic solvent gradient. Preferably, the isocratic elution is with four column volumes of 0.2 M acetic acid containing 19% ethanol, and the gradient (step or linear) from 19% to 25% ethanol (v/v), in 0.2 M acetic acid. Contaminating materials more hydrophobic than authentic IGF-I remain adsorbed to the column and are thereby separated from the authentic IGF-I. The ethanol gradient may be a step gradient or a linear gradient.

Following elution of the authentic IGF-I, remaining adsorbed compounds, i.e., those that are the more hydrophobic than authentic IGF-I, are "stripped" (removed) from the reverse phase column. Preferably, the column is stripped with a high concentration of ethanol, i.e., a concentration between about 70% and 100%.

Concentration/Diafiltration

Following the reverse phase chromatography step, the purified authentic IGF-I is subjected to a concentration procedure involving ultrafiltration. The intent in this step is to concentrate the purified IGF-I to a final concentration of approximately 12–16 mg/ml and replace the reverse phase chromatography elution buffer with a buffer suitable for subsequent steps in formulating the final product.

Ultrafiltration membranes, made of various materials and having various pore sizes (which determine molecular weight cutoff), are commercially available. In a preferred embodiment of the invention, polysulfone flat membranes, with a 1,000 molecular weight cutoff (Filtron, Northborough, Mass.) may be used. In a more preferred embodiment, polysulfone hollow fiber membranes with a 3,000 or 5,000 molecular weight cutoff (AG Technology, Needham, Mass.) are used. The hollow fiber membranes have higher flux rates and better IGF-I retention capability than do the flat membranes, despite the difference in molecular weight cutoff specifications.

The concentration/diafiltration can be conducted at the conclusion of any, or all, of the foregoing steps in the process. For example, in cases where the purification of the material is to finished at different locations, concentration/diafiltration can be conducted after the HIC step. The needs of the artisan can dictate when the concentration/diafiltration step is carried out.

Analytical Procedures

At each step in the IGF-I purification process, aliquots of IGF-I-containing samples, IGF-I-depleted solutions, column washes, collected fractions, and the like are preferably assayed by one or more analytical procedures. Such assays allow selected aspects of the purification process to be monitored. The appropriate assay for a given sample will depend on the type of sample and the information sought. For example, it may be desirable to assay IGF-I, or contaminants, or both.

Various IGF-I analytical methods are known, including, for example, SDS-PAGE, isoelectric focusing, Western blotting, peptide mapping, N-terminal amino acid sequencing, and HPLC. Preferred IGF-I analytical methods for use in connection with this invention are HPLC methods, e.g., C4 RP HPLC, CS RP HPLC, cation exchange HPLC or SEC HPLC. One or more of these HPLC methods are typically used to assay chromatography column fractions throughout the IGF-I process.

Another preferred IGF-I analytical method is "cyano reverse phase chromatography" (YMC, Wilmington, N.C.). When using cyano reverse phase chromatography as an analytical method in connection with the present invention, a shallow gradient of acetonitrile with 0.1% trifluoroacetic acid ("TFA") is used to separate and quantitate authentic IGF-I and the major contaminating, non-authentic, forms of IGF-I.

Experimental Information

The prior art process, essentially as described in Holtz (supra), and the preferred process of this invention, were compared in experimental tests conducted on a 10-liter fermentation development scale. The IGF-I containing starting material consisted of the broth of 10-liter fermentation of *P. pastoris* strain GS115. That strain is stably transformed with plasmid pIGF206, which encodes recombinant human IGF-I with an N-terminal signal peptide. Due to the presence of the signal peptide, the recombinant human IGF-I is secreted into the *P. pastoris* growth medium. The growth medium and fermentation conditions were as described in Holtz (supra). PTM1 trace salt addition was reduced by 10-fold; furthermore, sulfuric acid, copper, zinc and iron levels in PTML were reduced by approximately 3-fold.

Figure 2:
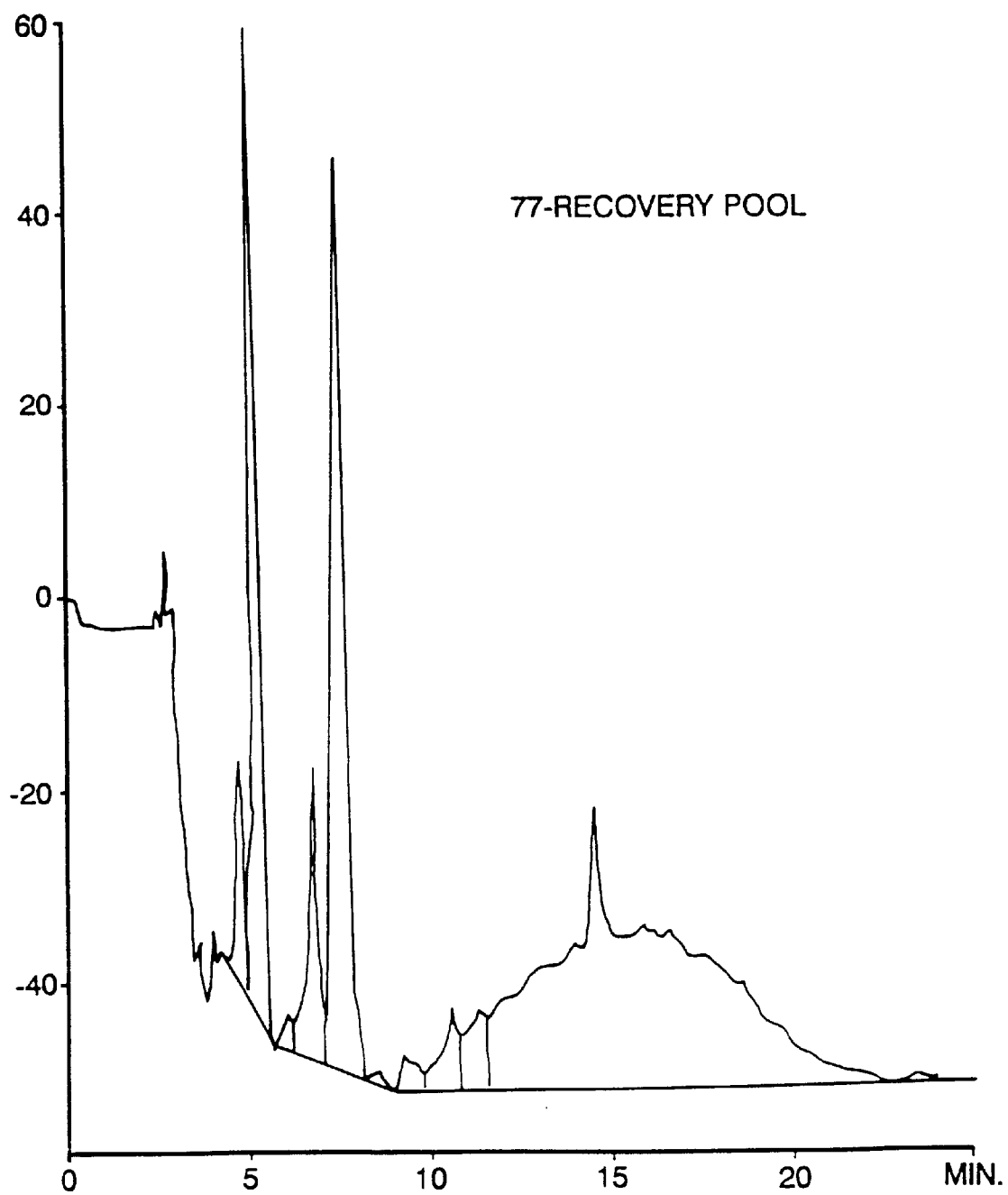
FIG. 2 is a typical analytical scale cyano reverse phase chromatogram of material recovered from the first cation exchange step of the Holtz process.

During the fermentation, several forms of IGF-I were secreted into the growth medium. FIG. 2 shows a typical cyano reverse phrase chromatogram of the IGF-I recovered from the first cation exchange step. These IGF-I forms include authentic IGF-I (approximately 18% of the total IGF-I) eluting at 7.3 minutes; misfolded monomeric IGF-I (approximately 15%) eluting at 5.08 minutes; degraded or amino-terminal clipped (des-2) monomer form (approximately 1% of total) eluting at 6.0 minutes; oxidized and glycosylated monomer forms (approximately 7% of total) eluting at 6.7 minutes; a variety of degraded or nicked monomer forms (approximately 7% of total) eluting between 8 and 11 minutes; and numerous multimeric forms (approximately 50% of total) eluting between 11 and 22 minutes.

Table I compares the basic steps in the Holtz process with preferred steps in the process of this invention. Optimization changes to the steps in the Holtz process are summarized in Table II. Yields of authentic IGF-I (as determined by cyano reverse phrase chromatography analysis) at each step in the processes are shown in Table III. The data in Table III regarding the preferred process of this invention are average values representing six 10-liter production runs. The data in Table III relating to the prior art process are from one 10-liter production run.

TABLE I

Comparison of Holtz Process and Process of Invention

| Steps in Holtz Process | Steps in Process of Invention |
| --- | --- |
| FERMENTATION | FERMENTATION |
| CELL REMOVAL | CELL REMOVAL |
| FIRST CATION EXCHANGE RECOVERY | FIRST CATION EXCHANGE RECOVERY |
|  | REFOLD |
| HYDROPHOBIC INTERACTION CHROMATOGRAPHY | HYDROPHOBIC INTERACTION CHROMATOGRAPHY |
| SECOND CATION EXCHANGE CHROMATOGRAPHY | SECOND CATION EXCHANGE CHROMATOGRAPHY |
| CONCENTRATION |  |
| GEL FILTRATION | REVERSE PHASE CHROMATOGRAPHY |
| CONCENTRATION/ DIAFILTRATION | CONCENTRATION/ DIAFILTRATION |

TABLE II

| PROCESS STEP | CHANGES TO PROCESS STEPS |
| --- | --- |
| FERMENTATION | Trace salt addition reduced during fermentation to comport with EPA limits. |
| CELL REMOVAL | Replace microfiltration with centrifugation. Water used to wash cells instead of 0.02M acetate. |
| FIRST CATION EXCHANGE RECOVERY | 0.1M NaCl eliminated from pre-elution 0.05M Na acetate, pH 5.5 wash. |
| HYDROPHOBIC INTERACTION CHROMATOGRAPHY | 0.5M NH4SO3 + 0.4M NaCl replaced with 1.25M NaCl during load. 0.6M NH4SO3 salt replaced with 0.2M Acetate, 0.5M NaCl in wash step. 0.6 to 0M NH4SO3 gradient replaced with 0.2M Acetate, 0.25M NaCl wash. 0.05M NaPO4 elution buffer replaced with 0.2M Acetate, 0.02M NaCl. |
| SECOND CATION CHROMATOGRAPHY | First low pH (4.5) wash buffer eliminated. 0 to 0.4M NaCl gradient replaced with 0.1M NaCl step wash. |
| CONCENTRATION | The first concentration step may be eliminated because it is not needed for operation of reverse phase step. |
| CONCENTRATION/ DIAFILTRATION | Polysulfone 1K flat membranes replaced with polysulfone 5K hollow fiber membranes. |

TABLE III

Authentic IGF-I Yields for Holtz Process and Process of Invention (10L Development Scale)

| HOLTZ PROCESS | AUTHENTIC IGF-I (mg) | PROCESS OF INVENTION | AUTHENTIC IGF-I (mg) |
| --- | --- | --- | --- |
| FERMENTATION | 968* | FERMENTATION | 863* |
| FIRST CATION EXCHANGE | 906 | FIRST CATION EXCHANGE | 818 |
|  | na | REFOLD | 1880 |
| HIC | 538 | HIC | 1835 |
| SECOND CATION | 451 | SECOND CATION | 1454 |
| EXCHANGE CONCENTRATION | 415 | EXCHANGE |  |
| GEL FILTRATION | 328 | REVERSE PHASE | 996 |
| CONCENTRATION/ DIAFILTRATION | 211** | CONCENTRATION/ DIAFILTRATION | 1046 |

*Authentic IGF-I in Fermentation broth calculated using C4 reverse phase as opposed to cyano reverse phase.
**Due to lower product levels in the Holtz manufacturing process, lower than normal losses of product is observed for this step at this scale.

Following cell removal, the cell-free fermentation broth was loaded onto a 270 ml Toyopearl SP550C™ (Tosohaas, Philadelphia, Pa.) column (5 cm×14 cm), at a flow rate of 130 ml/min, at 20–25° C. The loaded column was first washed with approximately 3 column volumes of 0.02 M acetic acid and then washed with approximately 3 column volumes of 0.05 M sodium acetate (pH 5.5), at a flow rate of 130 ml/min, at 20–25° C. IGF-I was eluted from the column with four column volumes of 0.05 M sodium acetate (pH.5.5), 0.4 M sodium chloride. Material recovered from the first cation exchange step is summarized in Table IV.

TABLE IV

Cyano Reverse Phase HPLC Analysis of Material from First Cation Recovery Step

| | % Authentic | % Misfolded | % Des 2 | % Oxid/ Glyco | % Nicked | % Multimer |
| --- | --- | --- | --- | --- | --- | --- |
| Holtz Process | 17 | 14 | 0.8 | 4.8 | 6.6 | 56 |
| Present Invention | 14 | 12 | 1.5 | 4.9 | 3.5 | 64 |

Figure 3:
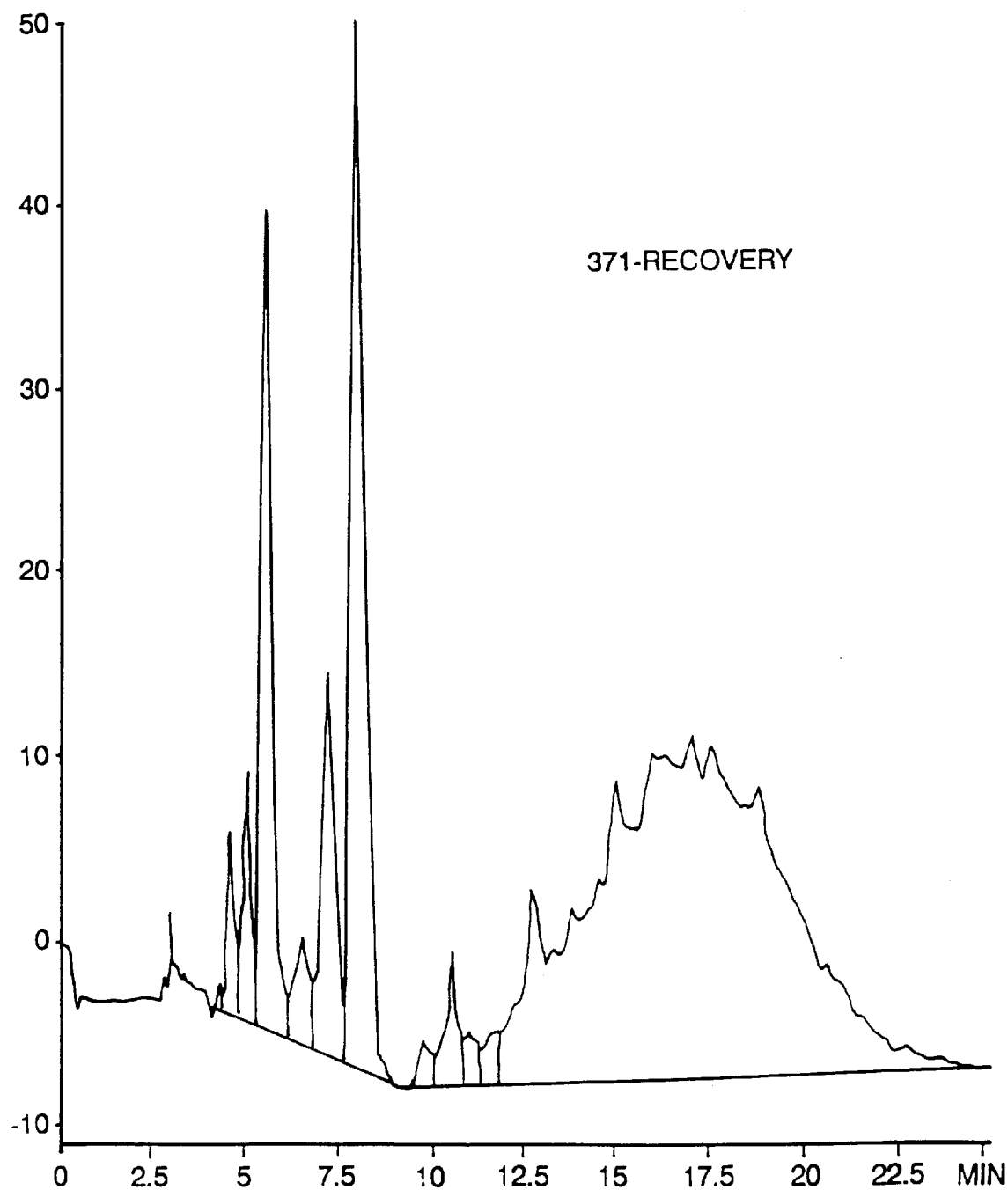
FIG. 3 is a typical analytical scale cyano reverse phase chromatogram of material recovered from the first cation exchange step of the invention.

The first cation exchange step in the process of this invention differs from the first cation exchange step in the Holtz process in that the sodium chloride in the second wash buffer has been removed. This advantageously permits recovery of the multimeric forms of IGF-I (which are converted to monomeric forms in the subsequent unfolding/refolding step). The increase in amount of multimeric IGF-I recovered is seen by comparing the analytical chromatograms of the Holtz first cation exchange ("SP1") product and the SP1 product obtained using the process of this invention. Except for the multimeric IGF-I levels, there are no significant differences between the two SP1 chromatography profiles (FIGS. 2 and 3).

Figure 4A:
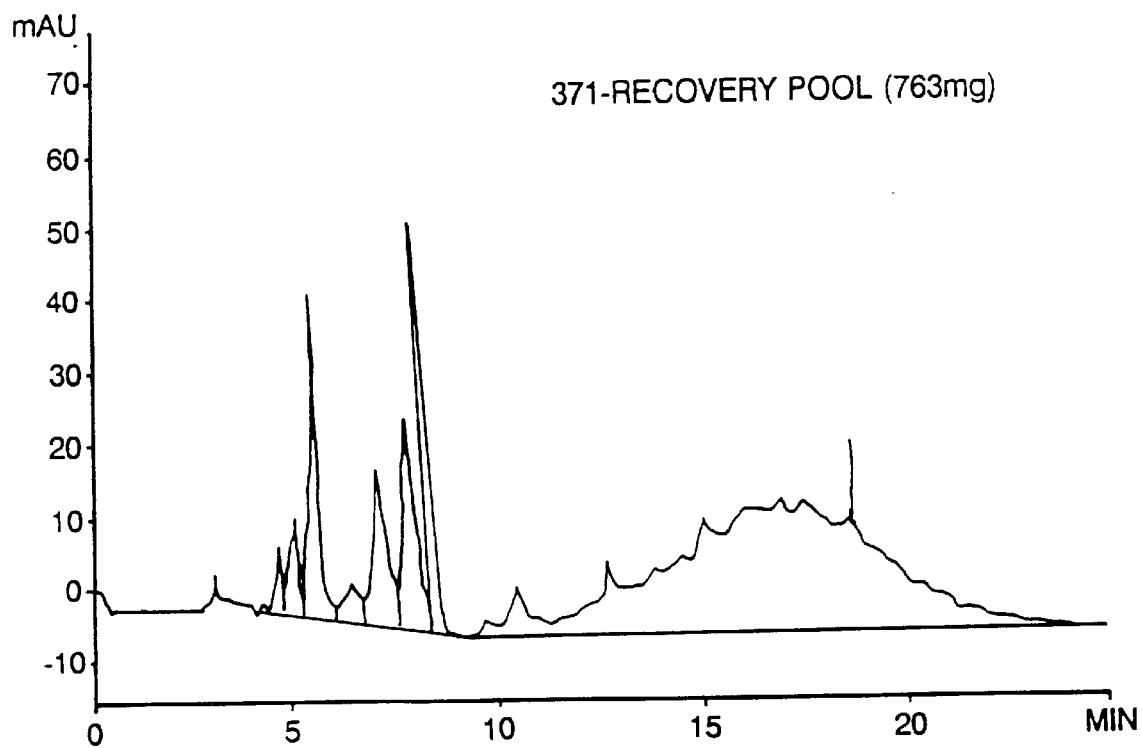
FIG. 4A is a typical analytical scale cyano reverse phase chromatogram of material recovered before the unfolding/refolding step in the invention.
Figure 4B:
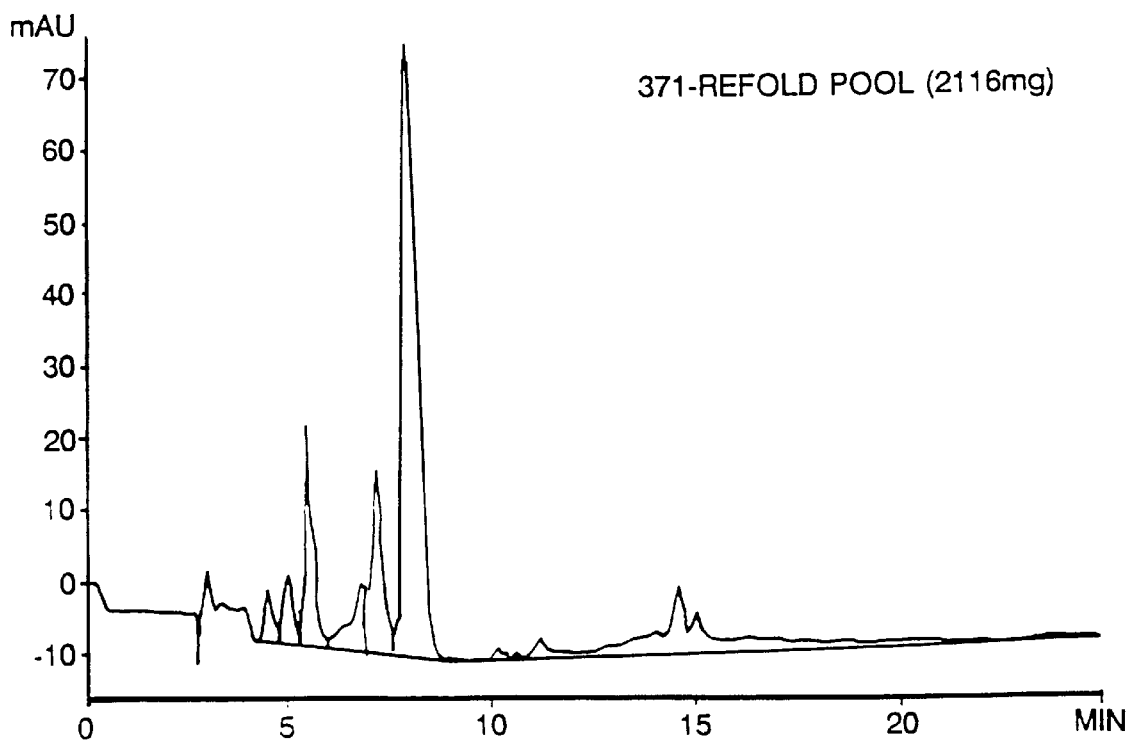
FIG. 4B is a typical analytical scale cyano reverse chromatogram of material recovered after the unfolding/refolding step in the process of the invention.

The SP1 recovery pool was combined with a concentrated (2× concentration) stock of unfold/refold buffer so as to yield the following final concentrations: 2 M urea, 1.5 M sodium chloride, 15% ethanol; 5 mM sodium borate; and 0.2 mM DTT (pH9–9.5). Unfolding/refolding was allowed to proceed, with gentle mixing, at room temperature for 15 to 20 hours. Typical cyano reverse phrase chromatograms from analyses done before and after the unfolding/refolding step are shown in FIGS. 4A and 4B. The relative amounts of the various forms of IGF-I (as a percentage of total IGF-I) before and after the unfolding/refolding step are presented in Table V. The reduction in multimeric IGF-I peaks and the increase in the authentic IGF-I peak are clearly visible in FIGS. 4A and 4B. As a result of the decreased multimeric peaks, authentic IGF-I was increased from 14% to 44% of the total IGF-I present. Since a high percentage of multimeric IGF-I is converted to monomeric (64% multimeric reduced to 21% multimeric) there is also an increase in the amount of some of the non-authentic monomeric forms. For example, oxidized and glycosylated forms (7.25 minutes) increased from 5% to 12% of the total; a degraded form designated des 2 (6.86 minutes) increased from 1.5% to 3.4% (Table V).

It should be noted, however, that the ratio of non-authentic monomeric forms to authentic IGF-I did not increase, because the amount of authentic IGF-I also increased. No new contaminants were identified as a result of the unfolding/refolding step. The unfold/refold process has been carried out in experiments corresponding to the 100-liter and 1500-liter fermentation scale, and comparable results were obtained (data not shown).

TABLE V

Cyano Reverse Phase HPLC Analysis of Material Before and After Unfolding/Refolding Step

| | % Authentic | % Misfolded | % Des 2 | % Oxid/ Glyco | % Nicked | % Multimer |
|---|---|---|---|---|---|---|
| Before | 14 | 12 | 1.5 | 4.9 | 3.5 | 64 |
| After | 44 | 16 | 3.4 | 12.1 | 1.7 | 21 |

In preparation for loading onto the HIC column, the pH of the refold pool was adjusted to 4.2 with acetic acid and then diluted with an equal volume of 1 M sodium chloride. The pH-adjusted refold pool, containing 1.25 M sodium chloride, was loaded onto the Toyopearl Butyl 650M™ (TosoHaas, Philadelphia, Pa.) HIC column (3.2 cm×47 cm) at 40 ml/min., at 20–25° C.

The HIC column, with adsorbed IGF-I, was washed with approximately three column volumes of 0.2 M acetic acid containing 0.5 M sodium chloride. The HIC column was then washed with approximately ten column volumes of 0.2 M acetic acid containing 0.25 M sodium chloride. The adsorbed IGF-I was then eluted from the HIC column with four column volumes of 0.2 M acetic acid, containing 0.02 M sodium chloride.

Figure 5A:
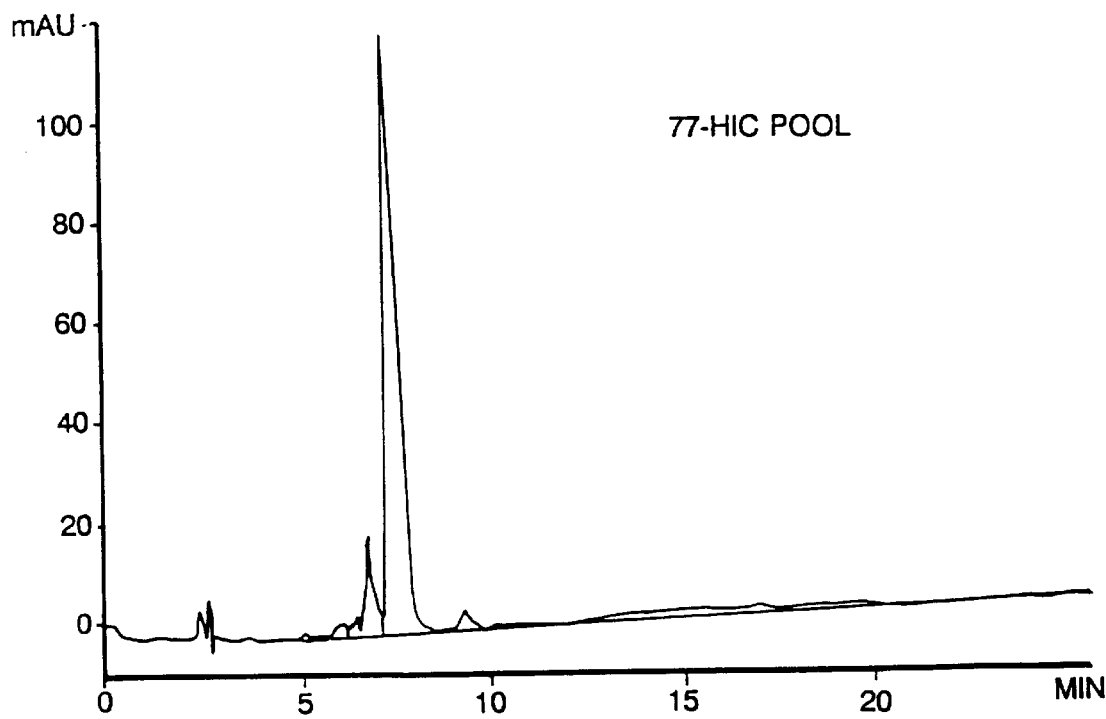
FIG. 5A is a typical analytical scale cyano reverse phase chromatogram of material recovered from the HIC step in the Holtz process.
Figure 5B:
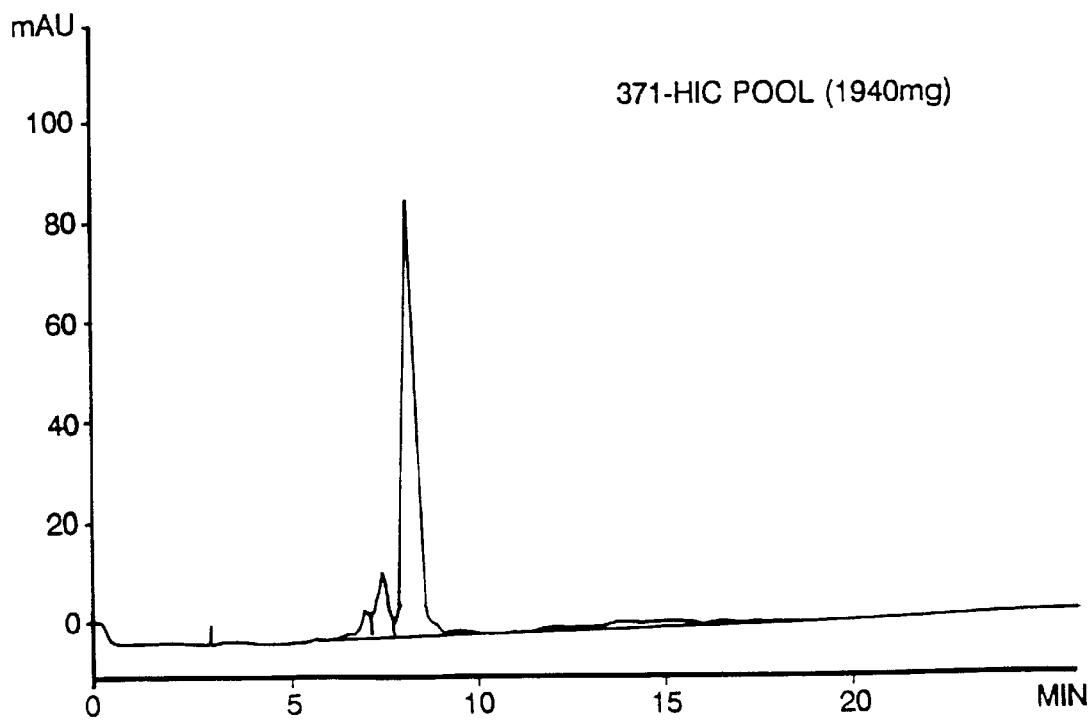
FIG. 5B is a typical analytical scale cyano reverse phase chromatogram of material recovered from the HIC step in the process of the invention.
Figure 6A:
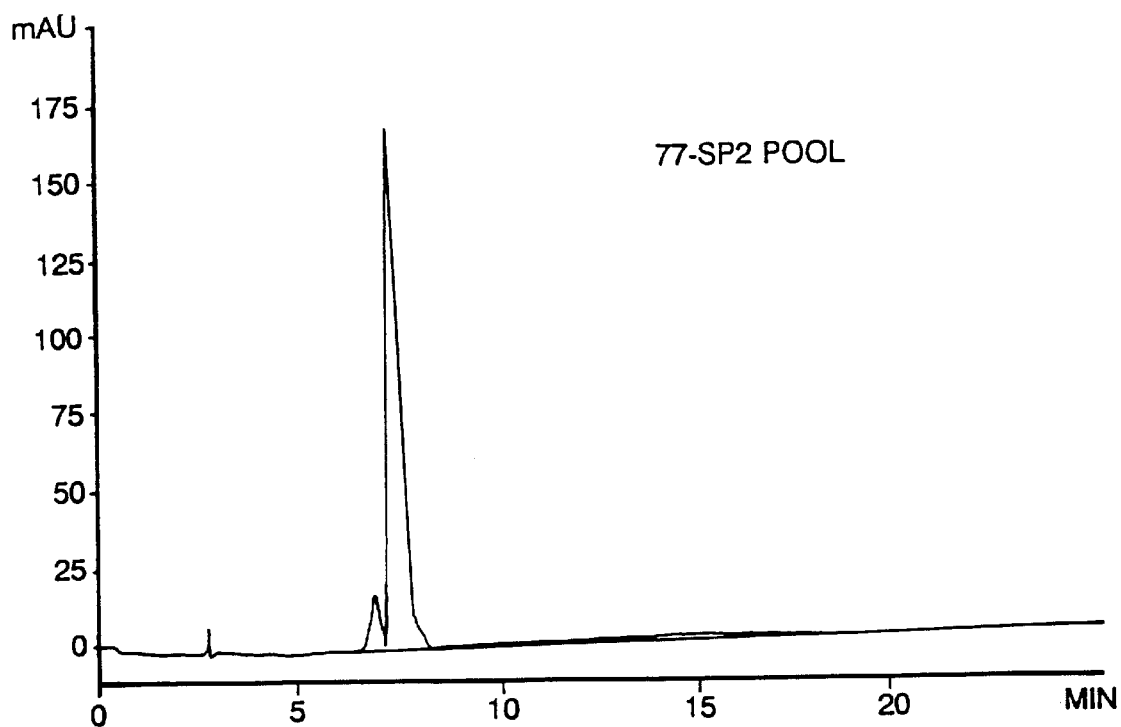
FIG. 6A is a typical analytical scale cyano reverse phase chromatogram of material recovered from the second cation exchange chromatography step in the Holtz process.
Figure 6B:
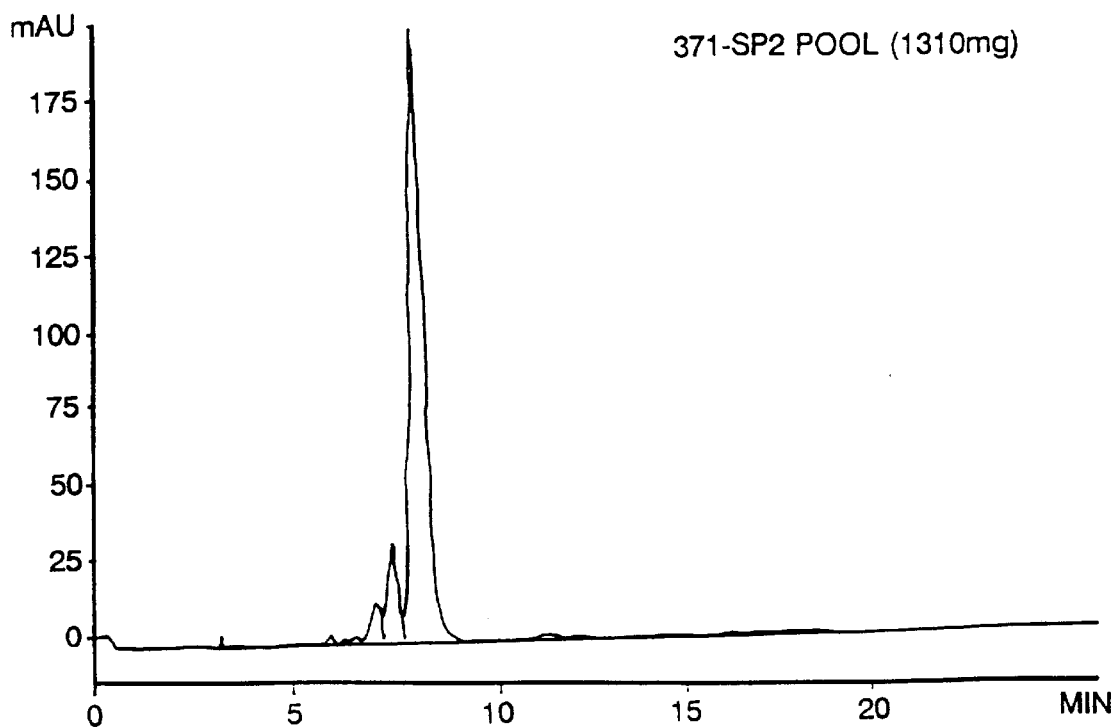
FIG. 6B is a typical analytical scale cyano reverse phase chromatogram of material recovered from the second cation exchange chromatography step in the invention.

Typical cyano reverse phase chromatograms from analysis of the product recovered after the HIC step are shown in FIGS. 5A and 5B. There is essentially no difference in the chromatographic profiles. The relative amounts of the various forms of IGF-I (as a percentage of total IGF-I) after the HIC step in the Holtz process and the process of this invention are presented in Table VI.

TABLE VI

Cyano Reverse Phase HPLC Analysis of Material from HIC Steps

| | % Authentic | % Misfolded | % Des 2 | % Oxid/ Glyco | % Nicked | % Multimer |
|---|---|---|---|---|---|---|
| Holtz Process | 64 | 1.1 | 1.9 | 9.5 | 3.0 | 19 |
| Present Invention | 71 | 1.1 | 4.2 | 10 | 1.7 | 11 |

The second cation exchange step was carried out on a Toyopearl SP550C (TosoHaas, Philadelphia, Pa.) column (1.6 cm×35 cm), at a flow rate of 10 ml/min.

After loading, the second cation exchange column was washed with approximately one column volume of 0.05 M sodium acetate buffer (pH 5.5). The column was then washed with approximately 7 column volumes of 0.05 M sodium acetate, 0.1 M sodium chloride (pH 5.5). The IGF-I was eluted with approximately 7 column volumes of 0.05 M sodium acetate, 0.4 M sodium chloride (pH 5.5). The relative amounts of the various forms of IGF-I (as a percentage of total IGF-I) after the second cation exchange step in the Holtz process and the process of this invention are presented in Table VII.

TABLE VII

Cyano Reverse Phase HPLC Analysis of Material from Second Cation Chromatography Step

| | % Authentic | % Misfolded | % Des 2 | % Oxid/ Glyco | % Nicked | % Multimer |
|---|---|---|---|---|---|---|
| Holtz Process | 82 | 0 | 0.9 | 6.6 | 1.6 | 8.7 |
| Present Invention | 84 | 1.0 | 3.7 | 9.9 | 0.7 | 0 |

Figure 7A:
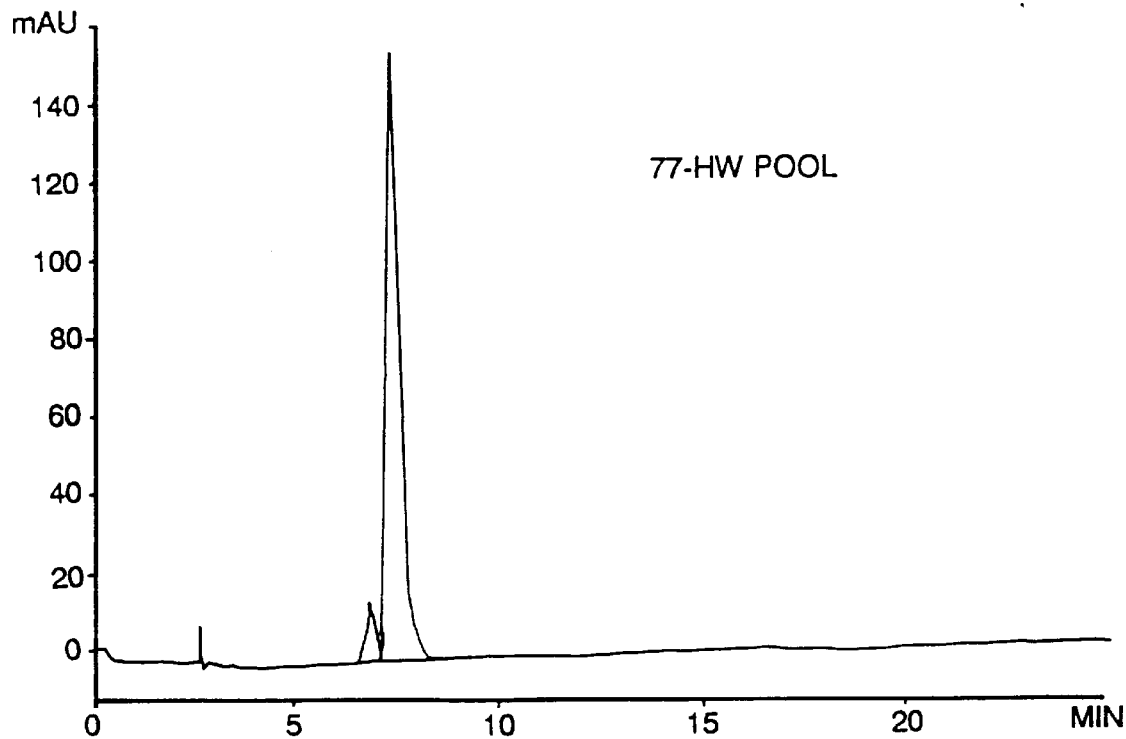
FIG. 7A is a typical analytical scale cyano reverse phase chromatogram of material recovered from the gel filtration chromatography step in the Holtz process.
Figure 7B:
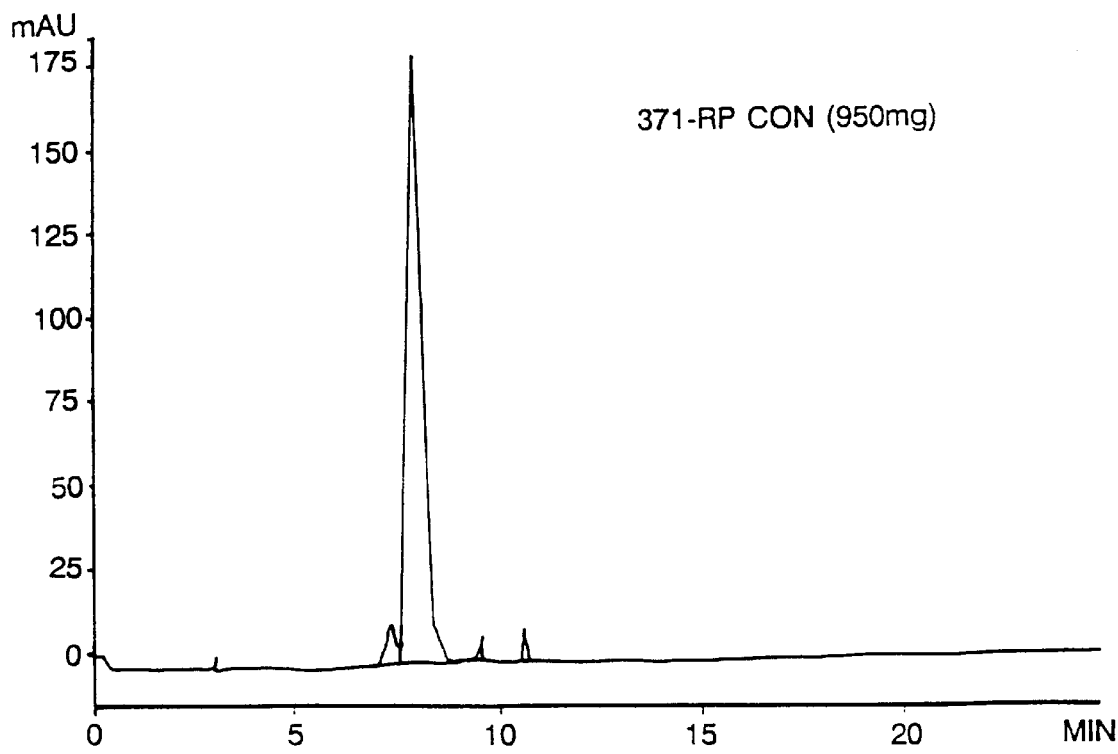
FIG. 7B is a typical analytical scale cyano reverse phase chromatogram of material recovered from the reverse phase chromatography step in the invention.

The material recovered from the second cation exchange step was loaded onto an Amberchrom CG1000sd™ (TosoHaas, Philadelphia, Pa.) reverse phase chromatography column (2.6 cm×21 cm), equilibrated with about 3 column volumes of 0.2 M acetic acid buffer (20 ml/min. flow rate). After loading, the reverse phase column was washed with one column volume of 0.2 M acetic acid. The column was then washed with four column volumes of 0.2 M acetic acid containing 19% ethanol (flow rate was reduced to 15 ml/min). The IGF-I was eluted from the reverse phase column using a 19% to 25% ethanol gradient. After IGF-I recovery, the column was stripped with a high concentration of ethanol (i.e., 70–100%). FIG. 7 shows typical cyano reverse phase chromatograms from analyses of the Holtz gel filtration product and the reverse phase product from the process of this invention. The relative amounts of the various forms of IGF-I (as a percentage of total IGF-I) after the gel filtration step in the Holtz process and the reverse phase chromatography step in the process of this invention are presented in Table VIII.

TABLE VIII

% Purity Profile from Cyano Reverse Phase HPLC of Final Chromatography Steps

| | % Authentic | % Misfolded | % Des 2 | % Oxid/ Glyco | % Nicked | % Multimer |
|---|---|---|---|---|---|---|
| Holtz Process | 92 | 0 | 0.9 | 6.5 | 0.5 | 0.2 |
| Present Invention | 94 | 0 | 0.6 | 4.4 | 1.1 | 0 |

Final Product Analysis and Characterization

In order to ensure purity, identity and potency of the final product obtained in the practice of this invention, various tests have been employed.

SDS-PAGE

The purity and identity of the product was determined by SDS-PAGE. The product of the process of this invention co-migrates with the reference standard from the Holtz process, and contains no detectable amount of higher molecular weight proteins (data not shown).

Western Blot/ELISA

Non-IGF-I proteins were measured by Western blot and ELISA assays. For this test, primary antibodies were raised against proteins recovered from the first cation exchange step of a negative control Pichia pastoris fermentation. The antibodies were used to probe for the presence of contaminating host cell proteins. The amount of contaminating host cell protein is approximately 10-fold less in the product from the process of the present invention, compared to the product from the Holtz process. Slot blot ELISA assays were used to make the quantitative determinations. Table IX summarizes the results of the ELISA determinations.

TABLE IX

Summary of Contaminating Yeast Protein Levels

| Lot No. | Process | Yeast Protein (ppm) |
|---|---|---|
| DC42 | Holtz | 100 |
| 363 | Present Invention | <5 |
| 364 | Present Invention | <5 |
| 371 | Present Invention | <10 |

Cyano Reverse Phase HPLC

Figure 8A:
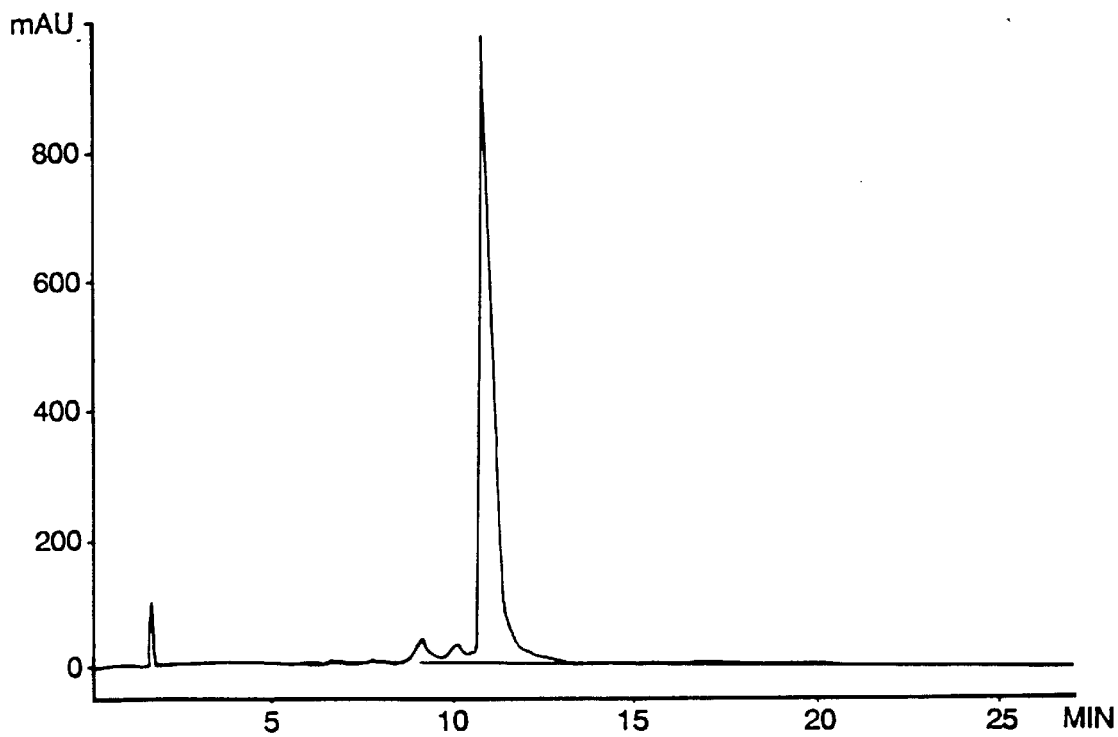
FIG. 8A is an analytical scale cyano reverse phase chromatogram of material produced by the Holtz process.
Figure 8B:
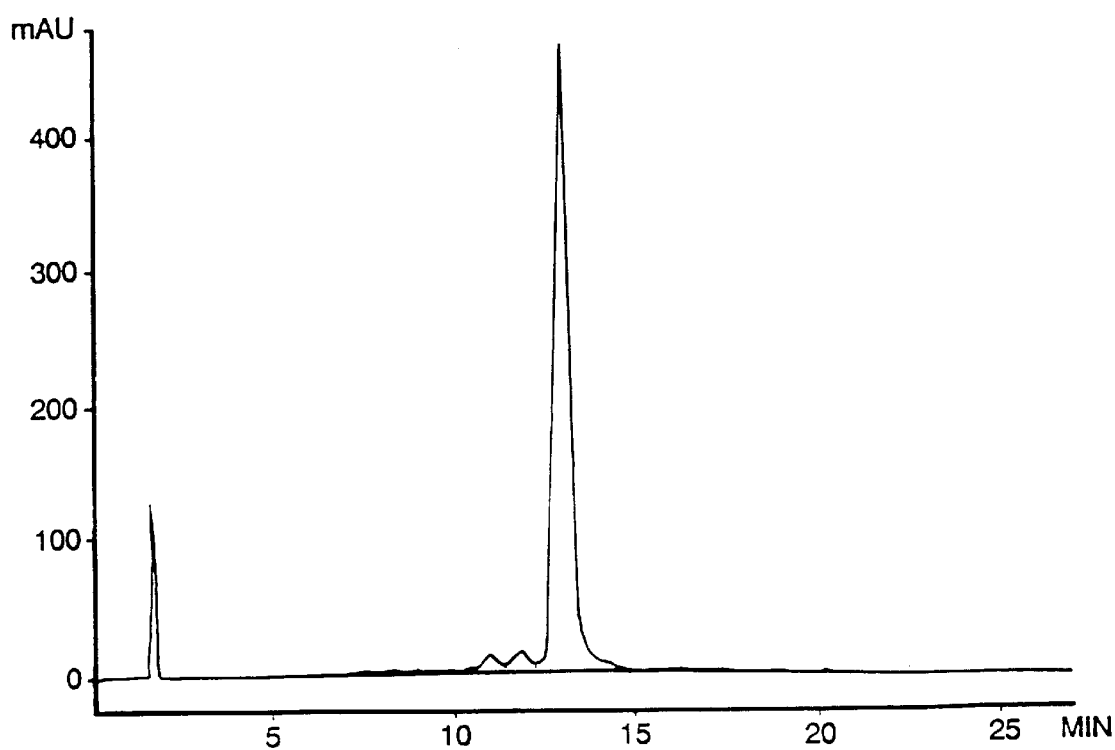
FIG. 8B is an analytical scale cyano reverse phase chromatogram of material purified by the process of the invention.
Figure 9A:
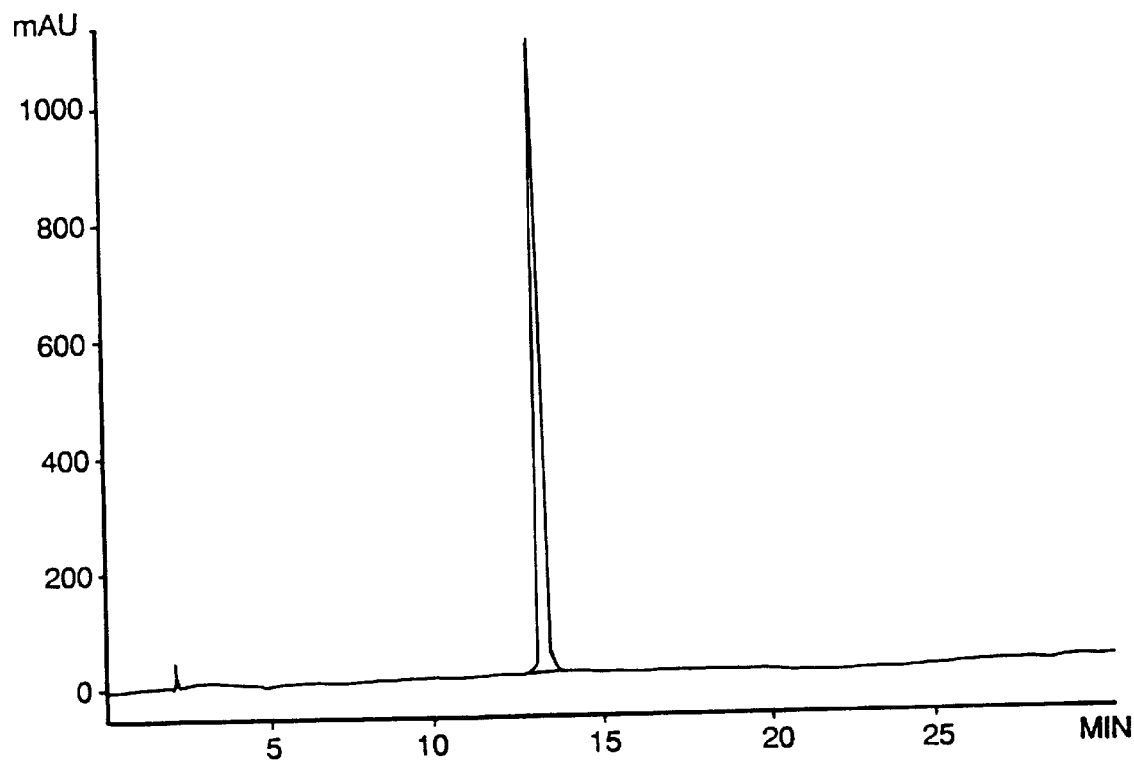
FIG. 9A is an analytical scale C8 reverse phase HPLC chromatogram of material purified by the Holtz process.
Figure 9B:
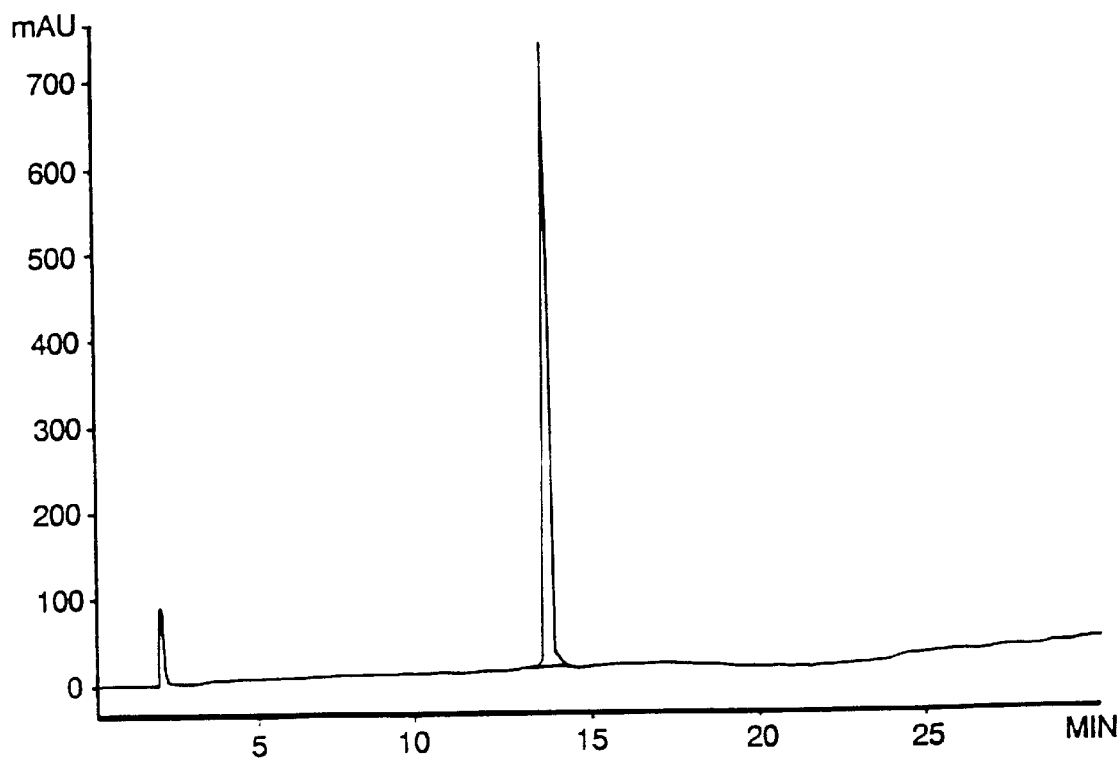
FIG. 9B is an analytical scale C8 reverse phase HPLC chromatogram of material purified by the process of the invention.

Final product purity was also evaluated using a cyano reverse phase column (Cyano Zorbax, MacMod Analytical, Chadds Ford, Pa.). A shallow gradient of acetonitrile with 25 mM phosphate buffer at pH 6.8 is used to separate the major IGF-I analogs and determine the concentration and purity of authentic IGF-I. This cyano reverse phase assay successfully resolves several IGF-I analogs (oxidized and glycosylated) from the authentic IGF-I. Table X summarizes the purity results for three lots of the material produced by the process of this invention, compared to several lots produced by the Holtz process. The reverse phase HPLC chromatogram in FIG. 8 shows the comparison between the Holtz process and the process of this invention.

TABLE X

Summary of Purity Data for Final Product
(as assessed by Phosphate Cyano Chromatography)

| Lot # | Process | % Authentic | % Mis-folded | % Oxidized | % Glyco-sylated | % Multimer |
|---|---|---|---|---|---|---|
| DC42 | Holtz | 91.0 | Not Det. | 4.4 | 3.0 | Not Det. |
| DC89 | Holtz | 91.6 | Not Det. | 2.9 | 2.6 | 0.6 |
| DC90 | Holtz | 91.9 | Not Det. | 2.7 | 2.3 | 0.6 |
| DC98 | Holtz | 92.1 | Not Det. | 2.4 | 2.7 | 0.6 |
| DC99 | Holtz | 93.1 | Not Det. | 2.4 | 2.2 | 0.5 |
| 363 | Present Invention | 92.3 | Not Det. | 2.8 | 3.4 | Not Det. |
| 364 | Present Invention | 92.08 | Not Det. | 2.5 | 4.1 | Not Det. |
| 371P | Present Invention | 93.2 | Not Det. | 2.7 | 3.0 | Not Det. |

Size Exclusion HPLC

Size exclusion HPLC is used to detect the presence of high molecular weight aggregates in the product. Table XI summarizes the results of the testing of each lot. The process of this invention effectively removes high molecular weight materials from the product.

TABLE XI

| Lot # | Process | % Authentic | % Multimer |
|---|---|---|---|
| DC42 | Holtz | 99.9 | 0.2 |
| DC89 | Holtz | 99.6 | 0.4 |
| DC90 | Holtz | 99.3 | 0.7 |
| DC98 | Holtz | 100 | Not Det. |
| DC99 | Holtz | 100 | Not Det. |
| 363 | Present Invention | 100 | Not Det. |
| 364 | Present Invention | 100 | Not Det. |
| 371 | Present Invention | 100 | Not Det. |
| 371P | Present Invention | 100 | Not Det. |

Isoelectric Focusing

Isoelectric focusing gels also confirm the identity of the products of the process of this invention, when compared to the products produced by the Holtz process (data not shown).

Protein Sequencing

N-terminal sequencing of the product confirmed the correct sequence of the protein, with respect to the product produced by the Holtz process and the published sequence of recombinant human IGF-I.

Peptide Mapping

Figure 10A:
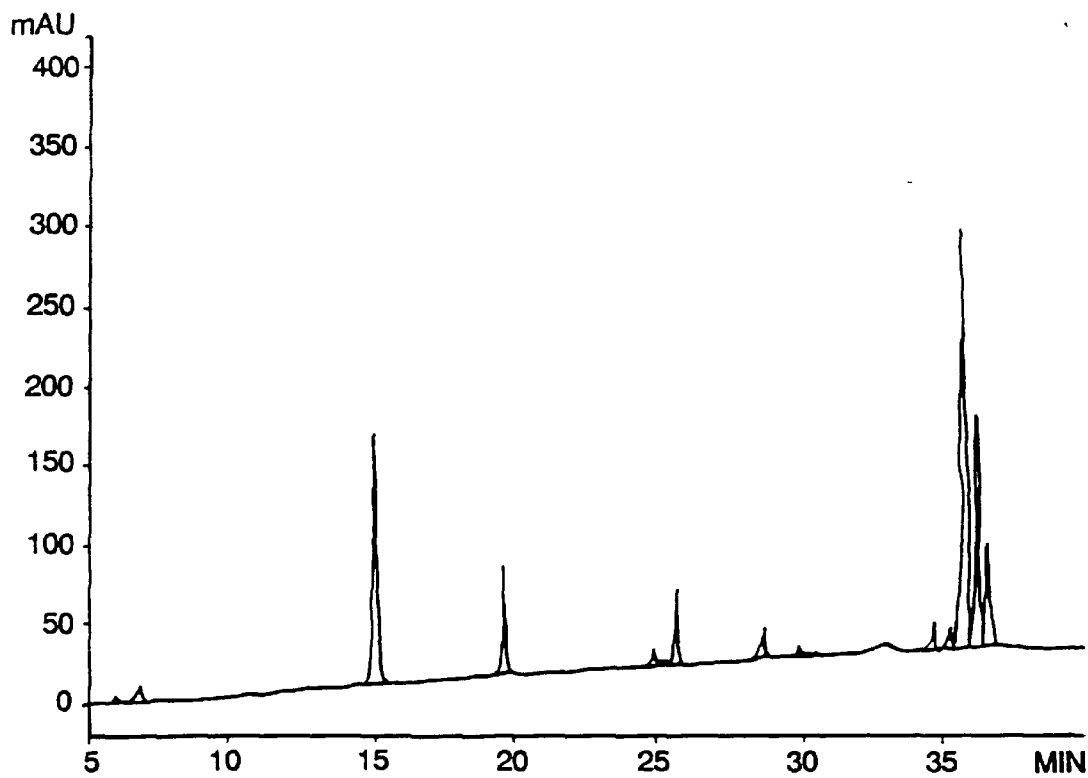
FIG. 10A is an analytical scale reverse phase chromatogram of peptide mapping products generated from reduced material purified by the Holtz process.
Figure 10B:
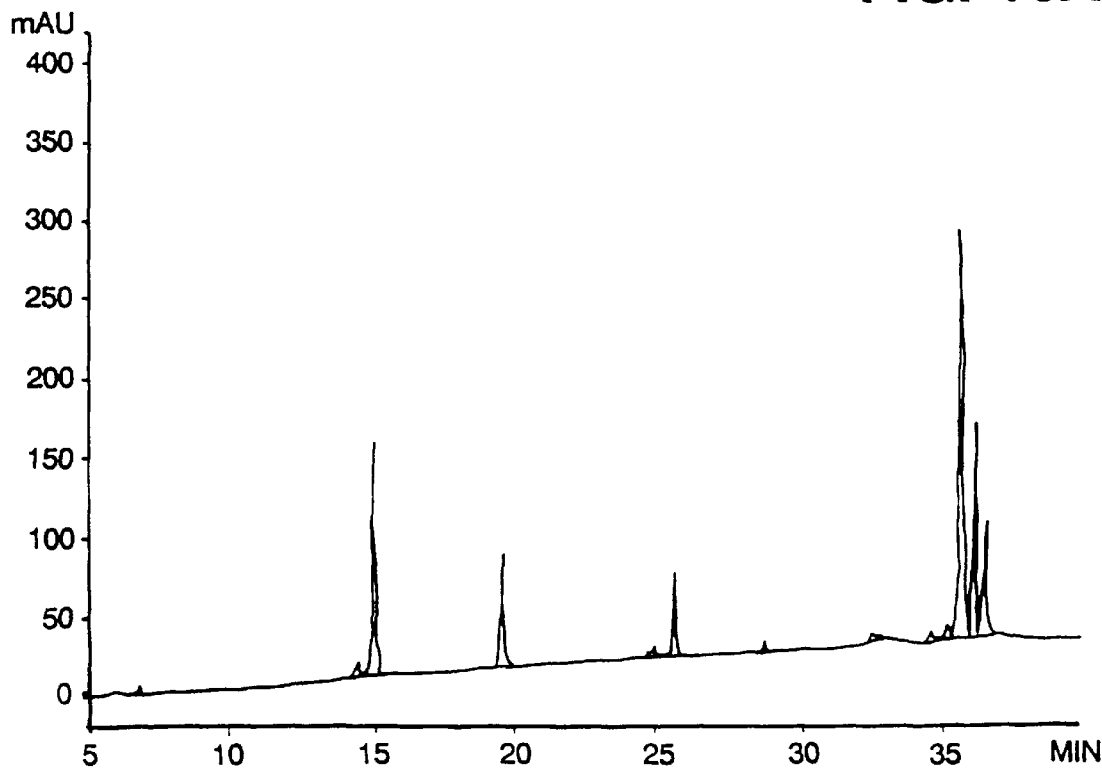
FIG. 10B is an analytical scale reverse phase chromatogram of peptide mapping products generated from reduced material purified by the process of the invention.
Figure 11A:
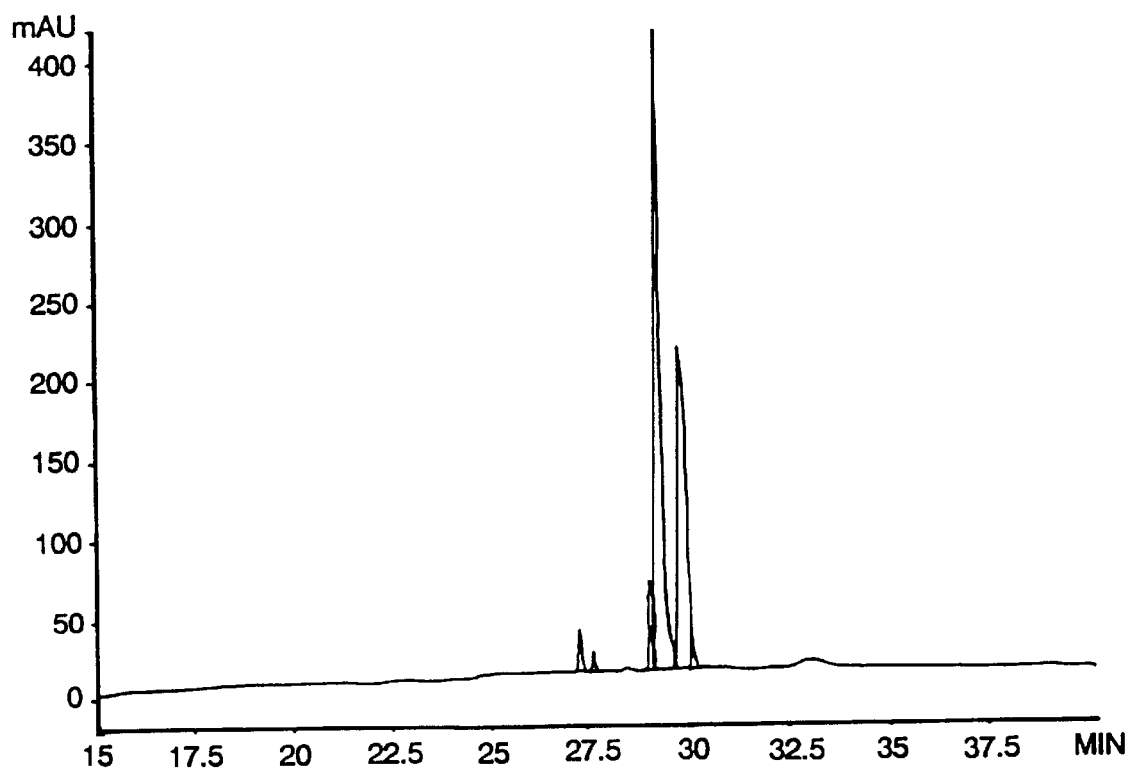
FIG. 11A is an analytical scale reverse phase chromatogram of peptide mapping products generated from non-reduced material purified by the Holtz process.
Figure 11B:
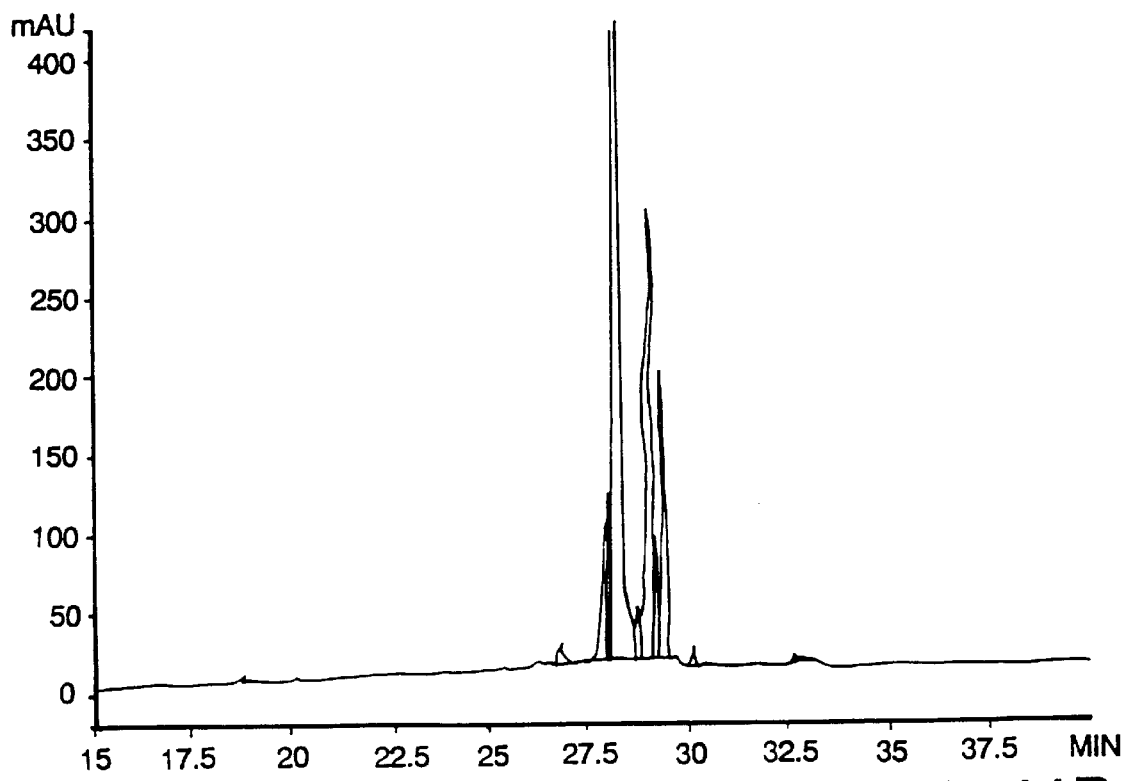
FIG. 11B is an analytical reverse phase chromatogram of peptide mapping products generated from non-reduced material purified by the process of the invention.
Figure 12A:
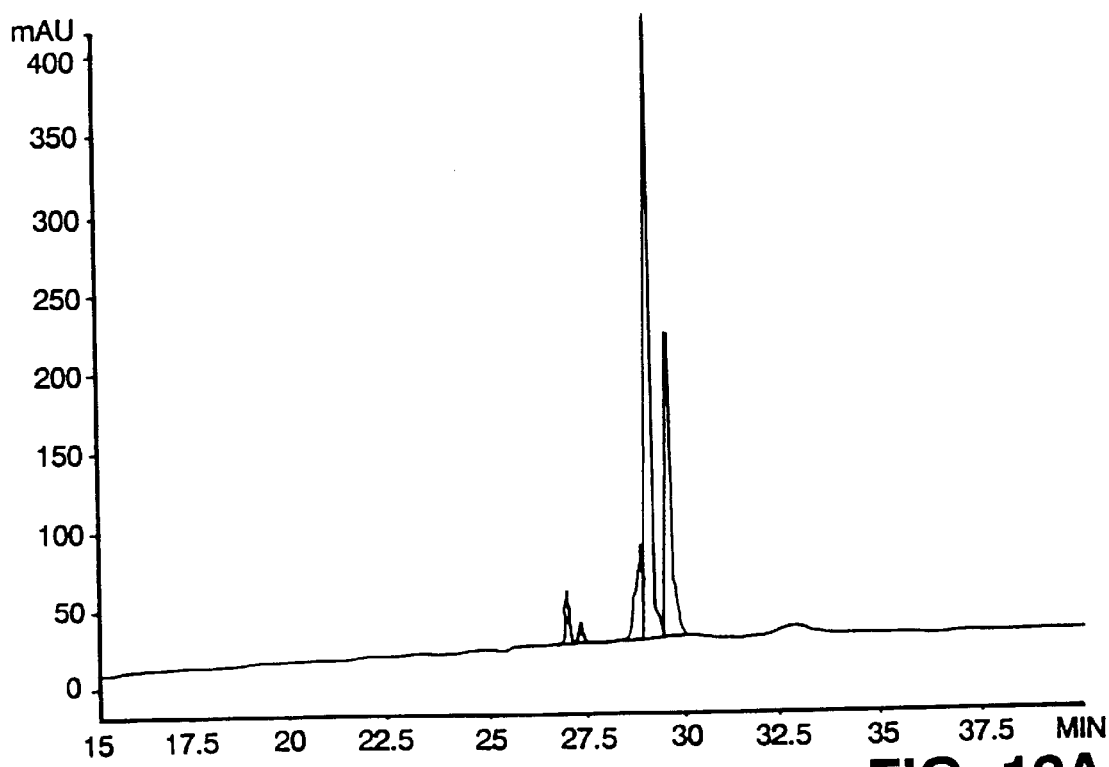
FIG. 12A is an analytical scale reverse phase chromatogram of peptide mapping products generated from correctly-folded non-reduced IGF-I.
Figure 12B:
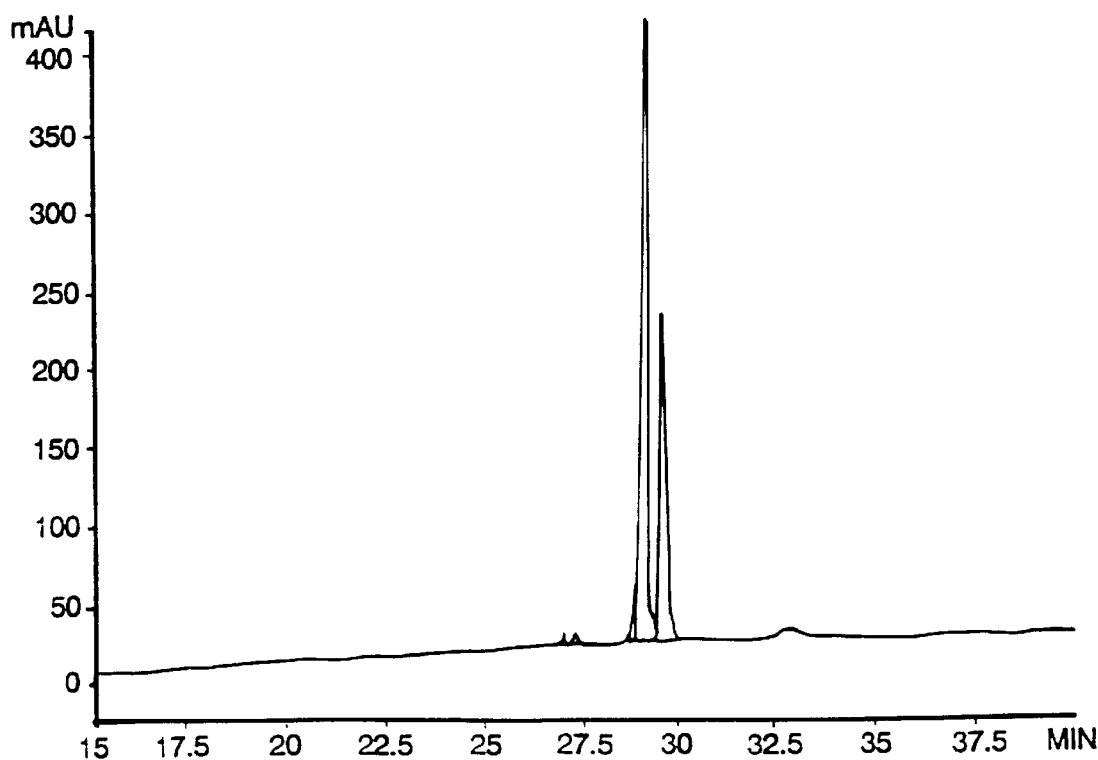
FIG. 12B is an analytical scale reverse phase chromatogram of peptide mapping products generated from misfolded non-reduced IGF-I.

Peptide mapping results for the product of this invention are identical to the results obtained with the Holtz process material. Both reduced and non-reduced maps match. FIG. 10 illustrates the results of the mapping studies. Because the product produced by the process of this invention is refolded, retention time of undigested IGF-I by RP-HPLC and on non-reduced peptide map peaks confirm the correct folding of the IGF-I produced by the process of this invention. In addition, FIG. 11 shows the peptide maps of misfolded IGF-I obtained from the purification process. As expected, the non-reduced map differs from the maps of the correctly folded authentic IGF-I.

Mass Spectroscopy

Further identity characterization, by mass spectroscopy, has been conducted. A major component, with a mass of 7649±5 AMU, was observed for each lot of material from the process of this invention. Minor components, of similar intensity to those in the Holtz process material, are also present.

Biological Activity

Radio receptor assay results for the material produced by the process of this invention agree well with the expected potency of the product, based on HPLC assays and total protein by ultraviolet spectroscopy.

The biological potency of the various lots of material produced by the process of this invention were also tested in a mitogenic bioassay. IGF-I is a potent mitogen. Its effect is measured by the incorporation of dimethylthiazol-2 yl diphenyltetrazolium (MT) into the DNA of the human osteosarcoma cell line MG-63. The potency of various lots of IGF-I produced by both processes are comparable (data not shown).

The products produced by the process of this invention have the expected characteristics of authentic rhIGF-I. The purity of the product has been increased by approximately 1–4% over the product from the Holtz process.

Other embodiments of this invention are within the following claims.

We claim:

1. A process for purifying authentic, properly folded monomeric insulin-like growth factor-I (IGF-I) from a medium containing IGF-I peptides, comprising the steps of:
    (a) contacting the medium with a sufficient quantity of a first cation exchange matrix under conditions allowing adsorption of substantially all forms of IGF-I from the medium;
    (b) washing the IGF-I-loaded first cation exchange matrix with a first cation exchange wash buffer which has a sufficiently low ionic strength to provide for retention of substantially all authentic and nonauthentic IGF-I forms by said matrix;
    (c) eluting substantially all forms of adsorbed IGF-I from the cation exchange matrix of step (a) by contacting said cation exchange matrix with a sufficient quantity of a first cation exchange elution buffer, which has a sufficiently high pH or ionic strength to displace substantially all of said authentic and non-authentic IGF-I forms from said cation exchange matrix;
    (d) transferring the IGF-I-forms-containing eluate from step (c) into an unfolding/refolding buffer, which:
        (i) reduces the intrachain disulfide bonds of IGF-I protein and promotes unfolding without permanent denaturation; and
        (ii) permits refolding of the IGF-I and reoxidation to form properly-paired intrachain disulfide bonds;
    (e) contacting the refolded IGF-I from step (d), after transfer into a suitable solvent system, with a sufficient quantity of a hydrophobic interaction chromatography matrix under conditions allowing adsorption of at least about 95% of said IGF-I from said eluate;
    (f) washing the IGF-I-loaded hydrophobic interaction chromatography matrix with a hydrophobic interaction wash buffer having an ionic strength sufficiently low to remove most of the non-authentic IGF-I from the hydrophobic interaction chromatography matrix while retaining substantially all of the adsorbed authentic IGF-I on said matrix;
    (g) eluting the adsorbed IGF-I from said hydrophobic interaction chromatography matrix by contacting said matrix with a hydrophobic interaction elution buffer, which has a sufficiently elevated pH, or sufficiently low ionic strength, to cause displacement of substantially all of the adsorbed authentic IGF-I from said matrix;
    (h) contacting the eluate from step (g) with a sufficient quantity of a second cation exchange matrix under conditions allowing adsorption of IGF-I from the eluate;
    (i) washing the IGF-I-loaded second cation exchange matrix with a cation exchange wash buffer having a sufficiently high ionic strength, or sufficiently high pH, to remove non-authentic IGF-I forms from said matrix while retaining substantially all of the adsorbed authentic IGF-I on said matrix;
    (j) eluting the adsorbed IGF-I from said second cation exchange matrix by contacting said matrix with a second cation exchange elution buffer, which has a sufficiently high ionic strength, or sufficiently high pH, to displace substantially all of the adsorbed authentic IGF-I from said matrix;
    (k) contacting the eluate from step (j), in an aqueous buffer, with a suitable quantity of a reverse phase chromatography matrix under conditions allowing adsorption of at least about 95% of the authentic IGF-I from the eluate;
    (l) washing the IGF-I-loaded reverse phase chromatography matrix with an aqueous/organic reverse phase wash buffer having an organic solvent concentration sufficiently high to remove non-authentic IGF-I forms from said matrix while retaining substantially all of the adsorbed authentic IGF-I on said matrix;
    (m) eluting the adsorbed IGF-I from said reverse phase chromatography matrix with an aqueous/organic buffer having an organic solvent concentration high enough to remove substantially all of the authentic IGF-I without removing substantially all of the non-authentic forms of IGF-I from said matrix.

2. The process of claim 1, wherein the non-authentic IGF-I removed by the washing in step (f) is reprocessed at least once through steps (d) to (g), inclusive, prior to initiation of step (h).

3. The process of claim 1, wherein said IGF-I is human recombinant IGF-I.

4. The process of claim 3, wherein said human recombinant IGF-I is produced in transformed yeast cells.

5. The process of claim 4, wherein said transformed yeast cells are of the species *Pichia pastoris*.

6. The process of claim 5, wherein said species *Pichia pastoris* is of the strain GS115.

7. The process of claim 4, wherein said IGF-I is secreted into the yeast growth medium.

8. The process of claim 1, part (a), wherein said first cation exchange matrix is sulfylpropylated and in a chromatography column.

9. The process of claim 1, part (b), wherein said washing consists essentially of applying to said first cation exchange matrix approximately 3.0 column volumes of 0.02 M acetic acid, followed by approximately 3.0 column volumes of 0.05 M sodium acetate (pH 5.5).

10. The process of claim 1, part (c), wherein said eluting consists essentially of applying to said first cation exchange matrix between 3 and 10 column volumes of 0.05 M sodium acetate (pH 5.5) and 0.4 M sodium chloride.

11. The process of claim 1, part (d) wherein said unfolding/refolding buffer consists essentially of: between about 1.5 and 3.0 M urea; between about 1.0 and 3.0 M sodium chloride; between about 5% and 20% (v/v) ethanol; between about 1 mM and 15 mM sodium borate; and between about 0.005 mM and 10.0 mM dithiothreitol; and has a pH between about 8.5 and 10.0.

12. The process of claim 1, part (d) wherein said unfolding/refolding buffer consists essentially of 2 M urea, 1.5 mM sodium chloride, 15% ethanol, 5 mM sodium borate and 0.2 mM DTT and has a pH between about 9.0 and 9.5.

13. The process of claim 1, part (e), wherein said hydrophobic interaction chromatography matrix is a butyl-substituted, polymethacrylate matrix.

14. The process of claim 1, part (f), wherein said washing consists essentially of applying to said hydrophobic interaction chromatography matrix approximately three column volumes of 0.2 M acetic acid, containing 0.5 M sodium chloride; followed by approximately ten column volumes of 0.2 M acetic acid, containing 0.15 to 0.25 M sodium chloride.

15. The process of claim 1, part (g), wherein said eluting consists essentially of applying to said hydrophobic interaction chromatography matrix approximately four column volumes of 0.2 M acetic acid, containing 0 to 0.02 M sodium chloride, and having a pH of approximately 3.0.

16. The process of claim 1, part (h), wherein said second cation exchange matrix is sulfylpropylated and in a chromatography column.

17. The process of claim 1, part (i), wherein said washing consists essentially of applying to said second cation exchange matrix approximately seven to ten column volumes of 0.05 M sodium acetate buffer, containing 0.1 M NaCl, and having a pH of approximately 5.5.

18. The process of claim 1, part (j), wherein said second cation exchange elution buffer consists essentially of approximately seven column volumes of 0.05 M sodium acetate, 0.4 M sodium chloride, having a pH of approximately 5.5.

19. The process of claim 1, part (k), wherein said reverse phase chromatography matrix is a polymer resin medium.

20. The process of claim 1, part (l), wherein said washing consists essentially of applying approximately one column volume of 0.2 M acetic acid, containing 0% ethanol, followed by approximately 4 column volumes of 0.2 M acetic acid, containing 19% ethanol.

21. The process of claim 1, part (m), wherein said eluting consists essentially of applying to said reverse phase chromatography matrix approximately four column volumes of 0.2 M acetic acid, containing 19% ethanol, followed by a gradient of 19% to 25% ethanol (v/v), in 0.2 M acetic acid, wherein the gradient is selected from the group consisting of linear gradient and step gradient.

22. A method for refolding an insulin-like growth factor-I (IGF-I) polypeptide derived from a yeast cell medium to yield an authentic, properly folded IGF-I polypeptide, wherein the method comprises: (a) isolating an IGF-I mixture from said yeast cell medium; and (b) denaturing and renaturing IGF-I species present in the IGF-I mixture from said yeast cell medium by adding an unfolding/refolding buffer which comprises about 1.5 to about 3 M urea, about 1 mM to about 15 mM sodium borate, about 1 M to about 3 M sodium chloride, about 5% to about 20% ethanol and about 0.005 mM to about 10 mM dithiothreitol, under conditions which allow for the reduction and subsequent oxidation of disulfide bonds, thereby producing an authentic, properly folded IGF-I polypeptide.

23. The method of claim 22, wherein the denaturation buffer has a pH of about 8.5 to about 10 and comprises about 2 M urea, about 5 mM sodium borate, about 1.5 M sodium chloride, about 15% ethanol, and about 0.2 mM dithiothreitol.

24. The method of claim 23, wherein the denaturation buffer has a pH of about 9.0 to about 9.5.

25. The method of claim 24, wherein the denaturing and renaturing are done together and conducted for about 15 hours to about 20 hours at room temperature.

* * * * *